United States Patent
Hirschberg et al.

(12) 
(10) Patent No.: US 6,218,599 B1
(45) Date of Patent: *Apr. 17, 2001

(54) **POLYNUCLEOTIDE MOLECULE FROM *HAEMATOCOCCUS PLUVIALIS* ENCODING A POLYPEPTIDE HAVING A β-C-4-OXYGENASE ACTIVITY FOR BIOTECHNOLOGICAL PRODUCTION OF (3S, 3'S) ASTAXANTHIN AND ITS SPECIFIC EXPRESSION IN CHROMOPLASTS OF HIGHER PLANTS**

(75) Inventors: Joseph Hirschberg, Jerusalem; Tamar Lotan, Kineret, both of (IL)

(73) Assignee: Yissum Research and Development Company of the Hebrew University of Jerusalem, Jerusalem (IL)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/259,294

(22) Filed: Mar. 1, 1999

Related U.S. Application Data

(63) Continuation of application No. 08/742,605, filed on Oct. 28, 1996, now Pat. No. 5,965,798, which is a continuation-in-part of application No. 08/562,535, filed on Nov. 24, 1995, now Pat. No. 5,916,791.

(30) Foreign Application Priority Data

Oct. 3, 1997 (WO) ................................ PCT/US97/17819

(51) Int. Cl.[7] .......................... A01H 11/00; C07H 21/02; C07H 21/04; C12N 1/20; C12N 1/14; C12N 5/00

(52) U.S. Cl. .................... 800/295; 800/298; 435/189; 435/252.3; 435/252.33; 435/254.11; 435/410; 435/320.1; 536/23.1; 536/23.2; 536/23.74

(58) Field of Search .................... 435/189, 328, 435/410, 423, 252.3, 252.33, 320.1, 254.11, 183, 254.21; 536/23.2, 23.74; 800/295, 298

(56) References Cited

FOREIGN PATENT DOCUMENTS

96/06172    7/1995   (WO).

OTHER PUBLICATIONS

Krinsky, N., "Antioxidant Functions of Carotenoids", *Free Radical Biol. & Medicine*, 7:617–635, 1989.

Demmig–Adams, B., "Carotenoids and Photoprotection in Plants: A Role for the Xanthophyll Zeaxanthin", *Biochimica et Biophysica Acta.*, 1020 (1990) 1–24.

Harker et al, "Biosynthesis of Ketocarotenoids in Transgenic Cyanobacteria Expressing the Algal Gene for β–C–4–Oxygenase, crtO", *FEBS Letters*, 404: 129–134, 1997.

*Primary Examiner*—Nashaat T. Nashed

(57) ABSTRACT

The present invention relates, in general, to a biotechnological method for production of (3S,3'S) astaxanthin. In particular, the present invention relates to a peptide having a β-C-4-oxygenase activity; a DNA segment coding for this peptide; an RNA segments coding for this peptide; a recombinant DNA molecule comprising a vector and the DNA segment; a host cell or organism containing the above described recombinant DNA molecule or DNA segment; and to a method of biotechnologically producing (3S,3'S) astaxanthin or a food additive containing (3S,3'S) astaxanthin, using the host.

15 Claims, 11 Drawing Sheets

Fig. 2

```
              1         10        20        30        40        50
CRTOA.AMI   MQLAATVMLEQLTGSAEALREKEKEVAGSSDVLRTWATQYSLPSEESDAARPGLKNAY
            : :   : ::   ::  ::        : : ::::  :::::  :::  :::::::  ::  ::
CRTOJ.AMI   MHVASALMVEQK-GS-EA------AASSPDVLRAWATQYHMPSESSDAARPALKHAY
              1          10                20        30        40

60        70        80        90        100       110
CRTOA.AMI   KPPPSDTKGITMALRVIGSWAAVFLHAIFQIKLPTSLDQLHWLPVSDATAQLVSGTSSLL
            :::  ::  :::::::  :: :  ::::::::::  ::::  :::::::::  :::::   :  ::::
CRTOJ.AMI   KPPASDAKGITMALTIIGTWTAVFLHAIFQIRLPTSMDQLHWLPVSEATAQLLGGSSSLL
              50        60        70        80        90        100

120       130       140       150       160       170
CRTOA.AMI   DIVVVFFVLEFLYTGLFITTHDAMHGTIAMRNRQLNDFLGRVCISLYAWFDYNMLHRKHW
              :   ::  ::::::::::::::::::::::: :  :::::   ::   :::::::::::::   :::::::
CRTOJ.AMI   HIAAVFIVLEFLYTGLFITTHDAMHGTIALRHRQLNDLLGNICISLYAWFDYSMLHRKHW
              110       120       130       140       150       160

180       190       200       210       220       230
CRTOA.AMI   EHHNHTGEVCKDPDFHRGNPGIVPWFASFMSSYMSMWQFARLAWWTVVMQLLGAPMANLL
            ::::::::::::::::::::::::  ::::   ::::::::::::::::   ::::::::::: ::::   ::::::::::
CRTOJ.AMI   EHHNHTGEVCKDPDFHKGNPGLVPWFASFMSSYMSLWQFARLAWHAVVMQMLGAPMANLL
              170       180       190       200       210       220

240       250       260       270       280       290
CRTOA.AMI   VFMAAAPILSAFRLFYFGTYMPHKPEPGAASGSSPAVMNWWKSRTSQASDLVSFLT
            :::::::::::::::::::::::::::    :::::::::   :    ::  :     :  :::   ::::
CRTOJ.AMI   VFMAAAPILSAFRLFYFGTYLPHKPEPGPAAGSQ--VMAWFRAKTSEASDVMSFLT
              230       240       250       260       270       280

300       310       320       329
CRTOA.AMI   CYHFDLHWEHHRWPFAPWWELPNCRRLSGRGLVPA
            ::::::::::::::::::::::  ::  :::::::::::::::::
CRTOJ.AMI   CYHFDLHWEHHRWPFAPWWQLPHCRRLSCRGLVPALA
              290       300       310       320
```

Fig. 3 pBIB pPTBIB pPTCRTOBIB

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH:1761 base pairs
      (B) TYPE:nucleic acid
      (C) STRANDEDNESS:double
      (D) TOPOLOGY:linear (xi) SEQUENCE DESCRIPTION:SEQ ID NO: 1:

```
GGC ACG AGC TTG CAC GCA AGT CAG CGC GCG CAA GTC AAC ACC TGC CGG      48

TCC ACA GCC TCA AAT AAT AAA GAG CTC AAG CGT TTG TGC GCC TCG ACG      96

TGG CCA GTC TGC ACT GCC TTG AAC CCG CGA GTC TCC CGC CGC ACT GAC     144

TGC CAT AGC ACA GCT AGA CGA ATG CAG CTA GCA GCG ACA GTA ATG TTG     192

GAG CAG CTT ACC GGA AGC GCT GAG GCA CTC AAG GAG AAG GAG AAG GAG     240

GTT GCA GGC AGC TCT GAC GTG TTG CGT ACA TGG GCG ACC CAG TAC TCG     288

CTT CCG TCA GAA GAG TCA GAC GCG GCC CGC CCG GGA CTG AAG AAT GCC     336

TAC AAG CCA CCA CCT TCC GAC ACA AAG GGC ATC ACA ATG GCG CTA CGT     384

GTC ATC GGC TCC TGG GCC GCA GTG TTC CTC CAC GCC ATT TTT CAA ATC     432

AAG CTT CCG ACC TCC TTG GAC CAG CTG CAC TGG CTG CCC GTG TCA GAT     480

GCC ACA GCT CAG CTG GTT AGC GGC ACG AGC AGC CTG CTC GAC ATC GTC     528

GTA GTA TTC TTT GTC CTG GAG TTC CTG TAC ACA GGC TTT TTT ATC ACC     576

ACG CAT GAT GCT ATG CAT GGC ACC ATC GCC ATG AGA AAC AGG CAG CTT     624

AAT GAC TTC TTG GGC AGA GTA TGC ATC TCC TTG TAC GCC TGG TTT GAT     672

TAC AAC ATG CTG CAC CGC AAG CAT TGG GAG CAC CAC AAC CAC ACT GGC     720

GAG GTG GGC AAG GAC CCT GAC TTC CAC AGG GGA AAC CCT GGC ATT GTG     768

CCC TGG TTT GCC AGC TTC ATG TCC AGC TAC ATG TCG ATG TGG CAG TTT     816
```

-continued

```
GCG CGC CTC GCA TGG TGG ACG GTG GTC ATG CAG CTG CTG GGT GCG CCA      864
ATG GCG AAC CTG CTG GTG TTC ATG GCG GCC GCG CCC ATC CTG TCC GCC      912
TTC CGC TTG TTC TAC TTT GGC ACG TAC ATG CCC CAC AAG CCT GAG CCT      960
GGC GCC GCG TCA GGC TCT TCA CCA GCC GTC ATG AAC TGG TGG AAG TCG     1008
CGC ACT AGC CAG GCG TCC GAC CTG GTC AGC TTT CTG ACC TGC TAC CAC     1056
TTC GAC CTG CAC TGG GAG CAC CAC CGC TGG CCC TTC GCC CCC TGG TGG     1104
GAG CTG CCC AAC TGC CGC CGC CTG TCT GGC CGA GGT CTG GTT CCT GCC     1152
TAG CTG GAC ACA CTG CAG TGG GCC CTG CTG CCA GCT GGG CAT GCA GGT     1200
TGT GGC AGG ACT GGG TGA GGT GAA AAG CTG CAG GCG CTG CTG CCG GAC     1248
ACG CTG CAT GGG CTA CCC TGT GTA GCT GCC GCC ACT AGG GGA GGG GGT     1296
TTG TAG CTG TCG AGC TTG CCC CAT GGA TGA AGC TGT GTA GTG GTG CAG     1344
GGA GTA CAC CCA CAG GCC AAC ACC CTT GCA GGA GAT GTC TTG CGT CGG     1392
GAG GAG TGT TGG CA GTG TAG ATG CTA TGA TTG TAT CTT AAT GCT GAA     1440
GCC TTT AGG GGA GCG ACA CTT AGT GCT GGG CAG GCA ACG CCC TGC AAG     1488
GTG CAG GCA CAA GCT AGG CTG GAC GAG GAC TCG GTG GCA GGC AGG TGA     1536
AGA GGT GCG GGA GGG TGG TGC CAC ACC CAC TGG GCA AGA CCA TGC TGC     1584
AAT GCT GGC GGT GTG GCA GTG AGA GCT GCG TGA TTA ACT GGG CTA TGG     1632
ATT GTT TGA GCA GTC TCA CTT ATT CTT TGA TAT AGA TAC TGG TCA GGC     1680
AGG TCA GGA GAG TGA GTA TGA ACA AGT TGA GAG GTG GTG CGC TGC CCC     1728
TGC GCT TAT GAA GCT GTA ACA ATA AAG TGG TTC                        1761

(2) INFORMATION FOR SEQ ID NO: 2:

(i) SEQUENCE CHARACTERISTICS:
            (A) LENGTH:1761 bases
            (B) TYPE:nucleic acid
            (C) STRANDEDNESS:single
            (D) TOPOLOGY:linear (xi) SEQUENCE DESCRIPTION:SEQ ID NO: 2:

GGC ACG AGC UUG CAC GCA AGU CAG CGC GCG CAA GUC AAC ACC UGC CGG       48
UCC ACA GCC UCA AAU AAU AAA GAG CUC AAG CGU UUG UGC GCC UCG ACG       96
UGG CCA GUC UGC ACU GCC UUG AAC CCG CGA GUC UCC CGC CGC ACU GAC      144
UGC CAU AGC ACA GCU AGA CGA AUG CAG CUA GCA GCG ACA GUA AUG UUG      192
GAG CAG CUU ACC GGA AGC GCU GAG GCA CUC AAG GAG AAG GAG AAG GAG      240
GUU GCA GGC AGC UCU GAC GUG UUG CGU ACA UGG GCG ACC CAG UAC UCG      288
CUU CCG UCA GAA GAG UCA GAC GCG GCC CGC CCG GGA CUG AAG AAU GCC      336
UAC AAG CCA CCA CCU UCC GAC ACA AAG GGC AUC ACA AUG GCG CUA CGU      384
GUC AUC GGC UCC UGG GCC GCA GUG UUC CUC CAC GCC AUU UUU CAA AUC      432
AAG CUU CCG ACC UCC UUG GAC CAG CUG CAC UGG CUG CCC GUG UCA GAU      480
GCC ACA GCU CAG CUG GUU AGC GGC ACG AGC AGC CUG CUC GAC AUC GUC      528
GUA GUA UUC UUU GUC CUG GAG UUC CUG UAC ACA GGC CUU UUU AUC ACC      576
ACG CAU GAU GCU AUG CAU GGC ACC AUC GCC AUG AGA AAC AGG CAG CUU      624
AAU GAC UUC UUG GGC AGA GUA UGC AUC UCC UUG UAC GCC UGG UUU GAU      672
```

```
UAC AAC AUG CUG CAC CGC AAG CAU UGG GAG CAC CAC AAC CAC ACU GGC      720

GAG GUG GGC AAG GAC CCU GAC UUC CAC AGG GGA AAC CCU GGC AUU GUG      768

CCC UGG UUU GCC AGC UUC AUG UCC AGC UAC AUG UCG AUG UGG CAG UUU      816

GCG CGC CUC GCA UGG UGG ACG GUG GUC AUG CAG CUG CUG GGU GCG CCA      864

AUG GCG AAC CUG CUG GUG UUC AUG GCG GCC GCG CCC AUC CUG UCC GCC      912

UUC CGC UUG UUC UAC UUU GGC ACG UAC AUG CCC CAC AAG CCU GAG CCU      960

GGC GCC GCG UCA GGC UCU UCA CCA GCC GUC AUG AAC UGG UGG AAG UCG     1008

CGC ACU AGC CAG GCG UCC GAC CUG GUC AGC UUU CUG ACC UGC UAC CAC     1056

UUC GAC CUG CAC UGG GAG CAC CAC CGC UGG CCC UUC GCC CCC UGG UGG     1104

GAG CUG CCC AAC UGC CGC CGC CUG UCU GGC CGA GGU CUG GUU CCU GCC     1152

UAG CUG GAC ACA CUG CAG UGG GCC CUG CUG CCA GCU GGG CAU GCA GGU     1200

UGU GGC AGG ACU GGG UGA GGU GAA AAG CUG CAG GCG CUG CUG CCG GAC     1248

ACG CUG CAU GGG CUA CCC UGU GUA GCU GCC GCC ACU AGG GGA GGG GGU     1296

UUG UAG CUG UCG AGC UUG CCC AUG GAU GAA GCU GUA GUG GUG CAG         1344

GGA GUA CAC CCA CAG GCC AAC ACC CUU GCA GGA GAU GUC UUG CGU CGG     1392

GAG GAG UGU UGG GCA GUG UAG AUG CUA UGA UUG UAU CUU AAU GCU GAA     1440

GCC UUU AGG GGA GCG ACA CUU AGU GCU GGG CAG GCA ACG CCC UGC AAG     1488

GUG CAG GCA CAA GCU AGG CUG GAC GAG GAC UCG GUG GCA GGC AGG UGA     1536

AGA GGU GCG GGA GGG UGG UGC CAC ACC CAC UGG GCA AGA CCA UGC UGC     1584

AAU GCU GGC GGU GUG GCA GUG AGA GCU GCG UGA UUA ACU GGG CUA UGG     1632

AUU GUU UGA GCA GUC UCA CUU AUU CUU UGA UAU AGA UAC UGG UCA GGC     1680

AGG UCA GGA GAG UGA GUA UGA ACA AGU UGA GAG GUG GUG CGC UGC CCC     1728

UGC GCU UAU GAA GCU GUA ACA AUA AAG UGG UUC                         1761

(2) INFORMATION FOR SEQ ID NO: 3:

(i) SEQUENCE CHARACTERISTICS:
        (A) LENGTH:1761 base pairs
        (B) TYPE:nucleic acid
        (C) STRANDEDNESS:double
        (D) TOPOLOGY:linear (xi) SEQUENCE DESCRIPTION:SEQ ID NO: 3:

GGC ACG AGC TTG CAC GCA AGT CAG CGC GCG CAA GTC AAC ACC TGC CGG       48

TCC ACA GCC TCA AAT AAT AAA GAG CTC AAG CGT TTG TGC GCC TCG ACG       96

TGG CCA GTC TGC ACT GCC TTG AAC CCG CGA GTC TCC CGC CGC ACT GAC      144

TGC CAT AGC ACA GCT AGA CGA ATG CAG CTA GCA GCG ACA GTA ATG TTG      192
                        Met Gln Leu Ala Ala Thr Val Met Leu
                         1               5

GAG CAG CTT ACC GGA AGC GCT GAG GCA CTC AAG GAG AAG GAG AAG GAG      240
Glu Gln Leu Thr Gly Ser Ala Glu Ala Leu Lys Glu Lys Glu Lys Glu
 10              15              20              25

GTT GCA GGC AGC TCT GAC GTG TTG CGT ACA TGG GCG ACC CAG TAC TCG      288
Val Ala Gly Ser Ser Asp Val Leu Arg Thr Trp Ala Thr Gln Tyr Ser
         30              35              40

CTT CCG TCA GAA GAG TCA GAC GCG GCC CGC CCG GGA CTG AAG AAT GCC      336
Leu Pro Ser Glu Glu Ser Asp Ala Ala Arg Pro Gly Leu Lys Asn Ala
     45              50              55
```

```
TAC AAG CCA CCA CCT TCC GAC ACA AAG GGC ATC ACA ATG GCG CTA CGT      384
Tyr Lys Pro Pro Pro Ser Asp Thr Lys Gly Ile Thr Met Ala Leu Arg
        60                  65                  70

GTC ATC GGC TCC TGG GCC GCA GTG TTC CTC CAC GCC ATT TTT CAA ATC      432
Val Ile Gly Ser Trp Ala Ala Val Phe Leu His Ala Ile Phe Gln Ile
        75                  80                  85

AAG CTT CCG ACC TCC TTG GAC CAG CTG CAC TGG CTG CCC GTG TCA GAT      480
Lys Leu Pro Thr Ser Leu Asp Gln Leu His Trp Leu Pro Val Ser Asp
90                  95                  100                 105

GCC ACA GCT CAG CTG GTT AGC GGC ACG AGC AGC CTG CTC GAC ATC GTC      528
Ala Thr Ala Gln Leu Val Ser Gly Thr Ser Ser Leu Leu Asp Ile Val
                    110                 115                 120

GTA GTA TTC TTT GTC CTG GAG TTC CTG TAC ACA GGC CTT TTT ATC ACC      576
Val Val Phe Phe Val Leu Glu Phe Leu Tyr Thr Gly Leu Phe Ile Thr
                125                 130                 135

ACG CAT GAT GCT ATG CAT GGC ACC ATC GCC ATG AGA AAC AGG CAG CTT      624
Thr His Asp Ala Met His Gly Thr Ile Ala Met Arg Asn Arg Gln Leu
            140                 145                 150

AAT GAC TTC TTG GGC AGA GTA TGC ATC TCC TTG TAC GCC TGG TTT GAT      672
Asn Asp Phe Leu Gly Arg Val Cys Ile Ser Leu Tyr Ala Trp Phe Asp
155                 160                 165

TAC AAC ATG CTG CAC CGC AAG CAT TGG GAG CAC CAC AAC CAC ACT GGC      720
Tyr Asn Met Leu His Arg Lys His Trp Glu His His Asn His Thr Gly
                170                 175                 180              185

GAG GTG GGC AAG GAC CCT GAC TTC CAC AGG GGA AAC CCT GGC ATT GTG      768
Glu Val Gly Lys Asp Pro Asp Phe His Arg Gly Asn Pro Gly Ile Val
                190                 195                 200

CCC TGG TTT GCC AGC TTC ATG TCC AGC TAC ATG TCG ATG TGG CAG TTT      816
Pro Trp Phe Ala Ser Phe Met Ser Ser Tyr Met Ser Met Trp Gln Phe
        205                 210                 215

GCG CGC CTC GCA TGG TGG ACG GTG GTC ATG CAG CTG CTG GGT GCG CCA      864
Ala Arg Leu Ala Trp Trp Thr Val Val Met Gln Leu Leu Gly Ala Pro
220                 225                 230

ATG GCG AAC CTG CTG GTG TTC ATG GCG GCG GCG CCC ATC CTG TCC GCC      912
Met Ala Asn Leu Leu Val Phe Met Ala Ala Ala Pro Ile Leu Ser Ala
                235                 240                 245

TTC CGC TTG TTC TAC TTT GGC ACG TAC ATG CCC CAC AAG CCT GAG CCT      960
Phe Arg Leu Phe Tyr Phe Gly Thr Tyr Met Pro His Lys Pro Glu Pro
                250                 255                 260              265

GGC GCC GCG TCA GGC TCT TCA CCA GCC GTC ATG AAC TGG TGG AAG TCG     1008
Gly Ala Ala Ser Gly Ser Ser Pro Ala Val Met Asn Trp Trp Lys Ser
        270                 275                 280

CGC ACT AGC CAG GCG TCC GAC CTG GTC AGC TTT CTG ACC TGC TAC CAC     1056
Arg Thr Ser Gln Ala Ser Asp Leu Val Ser Phe Leu Thr Cys Tyr His
                285                 290                 295

TTC GAC CTG CAC TGG GAG CAC CAC CGC TGG CCC TTC GCC CCC TGG TGG     1104
Phe Asp Leu His Trp Glu His His Arg Trp Pro Phe Ala Pro Trp Trp
            300                 305                 310

GAG CTG CCC AAC TGC CGC CGC CTG TCT GGC CGA GGT CTG GTT CCT GCC     1152
Glu Leu Pro Asn Cys Arg Arg Leu Ser Gly Arg Gly Leu Val Pro Ala
        315                 320                 325

TAG CTG GAC ACA CTG CAG TGG GCC CTG CTG CCA GCT GGG CAT GCA GGT     1200

TGT GGC AGG ACT GGG TGA GGT GAA AAG CTG CAG GCG CTG CTG CCG GAC     1248

ACG CTG CAT GGG CTA CCC TGT GTA GCT GCC GCC ACT AGG GGA GGG GGT     1296

TTG TAG CTG TCG AGC TTG CCC CAT GGA TGA AGC TGT GTA GTG GTG CAG     1344

GGA GTA CAC CCA CAG GCC AAC ACC CTT GCA GGA GAT GTC TTG CGT CGG     1392
```

```
GAG GAG TGT TGG GCA GTG TAG ATG CTA TGA TTG TAT CTT AAT GCT GAA    1440

GCC TTT AGG GGA GCG ACA CTT AGT GCT GGG CAG GCA ACG CCC TGC AAG    1488

GTG CAG GCA CAA GCT AGG CTG GAC GAG GAC TCG GTG GCA GGC AGG TGA    1536

AGA GGT GCG GGA GGG TGG TGC CAC ACC CAC TGG GCA AGA CCA TGC TGC    1584

AAT GCT GGC GGT GTG GCA GTG AGA GCT GCG TGA TTA ACT GGG CTA TGG    1632

ATT GTT TGA GCA GTC TCA CTT ATT CTT TGA TAT AGA TAC TGG TCA GGC    1680

AGG TCA GGA GAG TGA GTA TGA ACA AGT TGA GAG GTG GTG CGC TGC CCC    1728

TGC GCT TAT GAA GCT GTA ACA ATA AAG TGG TTC                        1761
```

(2) INFORMATION FOR SEQ ID NO: 4:

(i) SEQUENCE CHARACTERISTICS:
        (A) LENGTH:329 amino acids
        (B) TYPE:amino acid
        (C) TOPOLOGY:linear (xi) SEQUENCE DESCRIPTION:SEQ ID NO: 4:

```
                    Met Gln Leu Ala Ala Thr Val Met Leu
                     1               5

Glu Gln Leu Thr Gly Ser Ala Glu Ala Leu Lys Glu Lys Glu
 10              15              20              25

Val Ala Gly Ser Ser Asp Val Leu Arg Thr Trp Ala Thr Gln Tyr Ser
                 30              35              40

Leu Pro Ser Glu Glu Ser Asp Ala Ala Arg Pro Gly Leu Lys Asn Ala
                 45              50              55

Tyr Lys Pro Pro Pro Ser Asp Thr Lys Gly Ile Thr Met Ala Leu Arg
                 60              65              70

Val Ile Gly Ser Trp Ala Ala Val Phe Leu His Ala Ile Phe Gln Ile
 75              80              85

Lys Leu Pro Thr Ser Leu Asp Gln Leu His Trp Leu Pro Val Ser Asp
 90              95             100             105

Ala Thr Ala Gln Leu Val Ser Gly Thr Ser Leu Leu Asp Ile Val
                110             115             120

Val Val Phe Phe Val Leu Glu Phe Leu Tyr Thr Gly Leu Phe Ile Thr
                125             130             135

Thr His Asp Ala Met His Gly Thr Ile Ala Met Arg Asn Arg Gln Leu
    140             145             150

Asn Asp Phe Leu Gly Arg Val Cys Ile Ser Leu Tyr Ala Trp Phe Asp
    155             160             165

Tyr Asn Met Leu His Arg Lys His Trp Glu His His Asn His Thr Gly
170             175             180             185

Glu Val Gly Lys Asp Pro Asp Phe His Arg Gly Asn Pro Gly Ile Val
                190             195             200

Pro Trp Phe Ala Ser Phe Met Ser Tyr Met Ser Met Trp Gln Phe
                205             210             215

Ala Arg Leu Ala Trp Trp Thr Val Val Met Gln Leu Gly Ala Pro
    220             225             230

Met Ala Asn Leu Leu Val Phe Met Ala Ala Pro Ile Leu Ser Ala
    235             240             245

Phe Arg Leu Phe Tyr Phe Gly Thr Tyr Met Pro His Lys Pro Glu Pro
250             255             260             265

Gly Ala Ala Ser Gly Ser Ser Pro Ala Val Met Asn Trp Trp Lys Ser
                270             275             280
```

-continued

```
Arg Thr Ser Gln Ala Ser Asp Leu Val Ser Phe Leu Thr Cys Tyr His
            285                 290                 295

Phe Asp Leu His Trp Glu His His Arg Trp Pro Phe Ala Pro Trp Trp
        300                 305                 310

Glu Leu Pro Asn Cys Arg Arg Leu Ser Gly Arg Gly Leu Val Pro Ala
    315                 320                 325
```

POLYNUCLEOTIDE MOLECULE FROM *HAEMATOCOCCUS PLUVIALIS* ENCODING A POLYPEPTIDE HAVING A β-C-4-OXYGENASE ACTIVITY FOR BIOTECHNOLOGICAL PRODUCTION OF (3S, 3'S) ASTAXANTHIN AND ITS SPECIFIC EXPRESSION IN CHROMOPLASTS OF HIGHER PLANTS

This is a continuation of U.S. patent application Ser. No. 08/742,605, filed Oct. 28, 1996, now U.S. Pat. No. 5,965,798, which is a continuation-in-part of U.S. patent application Ser. No. 08/562,535, filed Nov. 24, 1995 now U.S. Pat. No. 5,916,791.

FIELD AND BACKGROUND OF THE INVENTION

The present invention relates, in general, to a biotechnological method for production of (3S,3'S) astaxanthin. In particular, the present invention relates to a peptide having a β-C-4-oxygenase activity; a DNA segment coding for this peptide; an RNA segments coding for this peptide; a recombinant DNA molecule comprising a vector and the DNA segment; a host cell or organism containing the above described recombinant DNA molecule or DNA segment; and to a method of biotechnologically producing (3S,3'S) astaxanthin or a food additive containing (3S,3'S) astaxanthin, using the host.

Carotenoids, such as astaxanthin, are natural pigments that are responsible for many of the yellow, orange and red colors seen in living organisms. Carotenoids are widely distributed in nature and have, in various living systems, two main biological functions: they serve as light-harvesting pigments in photosynthesis, and they protect against photo-oxidative damage. These and additional biological functions of carotenoids, their important industrial role, and their biosynthesis are discussed hereinbelow.

As part of the light-harvesting antenna, carotenoids can absorb photons and transfer the energy to chlorophyll, thus assisting in the harvesting of light in the range of 450–570 nm [see, Cogdell R J and Frank H A (1987) How carotenoids function in photosynthestic bacteria. Biochim Biophys Acta 895: 63–79; Cogdell R (1988) The function of pigments in chloroplasts. In: Goodwin T W (ed) Plant Pigments, pp 183–255. Academic Press, London; Frank H A, Violette C A, Trautman J K, Shreve A P, Owens T G and Albrecht A C (1991) Carotenoids in photosynthesis: structure and photochemistry. Pure Appl Chem 63: 109–114; Frank H A, Farhoosh R, Decoster B and Christensen R L (1992) Molecular features that control the efficiency of carotenoid-to-chlorophyll energy transfer in photosynthesis. In: Murata N (ed) Research in Photosynthesis, Vol I, pp 125–128. Kluwer, Dordrecht; and, Cogdell R J and Gardiner A T (1993) Functions of carotenoids in photosynthesis. Meth Enzymol 214: 185–193]. Although carotenoids are integral constituents of the protein-pigment complexes of the light-harvesting antennae in photosynthetic organisms, they are also important components of the photosynthetic reaction centers.

Most of the total carotenoids is located in the light harvesting complex II [Bassi R, Pineaw B, Dainese P and Marquartt J (1993) Carotenoid binding proteins of photosystem II. Eur J Biochem 212: 297–302]. The identities of the photosynthetically active carotenoproteins and their precise location in light-harvesting systems are not known. Carotenoids in photochemically active chlorophyll-protein complexes of the thermophilic cyanobacterium Synechococcus sp. were investigated by linear dichroism spectroscopy of oriented samples [see, Breton J and Kato S (1987) Orientation of the pigments in photosystem II: low-temperature linear-dichroism study of a core particle and of its chlorophyll-protein subunits isolated from Synechococcus sp. Biochim Biophys Acta 892: 99–107]. These complexes contained mainly a β-carotene pool absorbing around 505 and 470 nm, which is oriented close to the membrane plane. In photochemically inactive chlorophyll-protein complexes, the β-carotene absorbs around 495 and 465 nm, and the molecules are oriented perpendicular to the membrane plane.

Evidence that carotenoids are associated with cyanobacterial photosystem (PS) II has been described [see, Suzuki R and Fujita Y (1977) Carotenoid photobleaching induced by the action of photosynthetic reaction center II: DCMU sensitivity. Plant Cell Physiol 18: 625–631; and, Newman P J and Sherman L A (1978) Isolation and characterization of photosystem I and II membrane particles from the blue-green alga *Synechococcus cedrorum*. Biochim Biophys Acta 503: 343–361]. There are two β-carotene molecules in the reaction center core of PS II [see, Ohno T, Satoh K and Katoh S (1986) Chemical composition of purified oxygen-evolving complexes from the thermophilic cyanobacterium Synechococcus sp. Biochim Biophys Acta 852: 1–8; Gounaris K, Chapman D J and Barber J (1989) Isolation and characterization of a D1/D2/cytochrome b-559 complex from Synechocystis PCC6803. Biochim Biophys Acta 973: 296–301; and, Newell R W, van Amerongen H, Barber J and van Grondelle R (1993) Spectroscopic characterization of the reaction center of photosystem II using polarized light: Evidence for β-carotene excitors in PS II reaction centers. Biochim Biophys Acta 1057: 232–238] whose exact function(s) is still obscure [reviewed by Satoh K (1992) Structure and function of PS II reaction center. In: Murata N (ed) Research in Photosynthesis, Vol. II, pp. 3–12. Kluwer, Dordrecht]. It was demonstrated that these two coupled β-carotene molecules protect chlorophyll P680 from photodamage in isolated PS II reaction centers [see, De Las Rivas J, Telfer A and Barber J (1993) 2-coupled β-carotene molecules protect P680 from photodamage in isolated PS II reaction centers. Biochim. Biophys. Acta 1142: 155–164], and this may be related to the protection against degradation of the D1 subunit of PS II [see, Sandmann G (1993) Genes and enzymes involved in the desaturation reactions from phytoene to lycopene. (abstract), 10th International Symposium on Carotenoids, Trondheim CL1-2]. The light-harvesting pigments of a highly purified, oxygen-evolving PS II complex of the thermophilic cyanobacterium Synechococcus sp. consists of 50 chlorophyll α and 7 β-carotene, but no xanthophyll, molecules [see, Ohno T, Satoh K and Katoh S (1986) Chemical composition of purified oxygen-evolving complexes from the thermophilic cyanobacterium Synechococcus sp. Biochim Biophys Acta 852: 1–8]. β-carotene was shown to play a role in the assembly of an active PS II in green algae [see, Humbeck K, Romer S and Senger H (1989) Evidence for the essential role of carotenoids in the assembly of an active PS II. Planta 179: 242–250].

Isolated complexes of PS I from *Phormidium luridum*, which contained 40 chlorophylls per P700, contained an average of 1.3 molecules of β-carotene [see, Thornber J P, Alberte R S, Hunter F A, Shiozawa J A and Kan K S (1976) The organization of chlorophyll in the plant photosynthetic unit. Brookhaven Symp Biology 28: 132–148]. In a preparation of PS I particles from Synechococcus sp. strain PCC 6301, which contained 130±5 molecules of antenna chlorophylls per P700, 16 molecules of carotenoids were detected [see, Lundell D J, Glazer A N, Melis A and Malkin R (1985) Characterization of a cyanobacterial photosystem I complex. J Biol Chem 260: 646–654]. A substantial content of β-carotene and the xanthophylls cryptoxanthin and isocryptoxanthin were detected in PS I pigment-protein complexes of the thermophilic cyanobacterium *Synechococcus elongatus* [see, Coufal J, Hladik J and Sofrova D (1989) The carotenoid content of photosystem 1 pigment-protein complexes of the cyanobacterium *Synechococcus elongatus*. Photosynthetica 23: 603–616]. A subunit protein-complex structure of PS I from the thermophilic cyanobacterium Synechococcus sp., which consisted of four polypeptides (of 62, 60, 14 and 10 kDa), contained approximately 10 β-carotene molecules per P700 [see, Takahashi Y, Hirota K and Katoh S (1985) Multiple forms of P700-chlorophyll α-protein complexes from Synechococcus sp.: the iron, quinone and carotenoid contents. Photosynth Res 6: 183–192]. This carotenoid is exclusively bound to the large polypeptides which carry the functional and antenna chlorophyll α. The fluorescence excitation spectrum of these complexes suggested that β-carotene serves as an efficient antenna for PS I.

As mentioned, an additional essential function of carotenoids is to protect against photooxidation processes in the photosynthetic apparatus that are caused by the excited triplet state of chlorophyll. Carotenoid molecules with π-electron conjugation of nine or more carbon-carbon double bonds can absorb triplet-state energy from chlorophyll and thus prevent the formation of harmful singlet-state oxygen radicals. In Synechococcus sp. the triplet state of carotenoids was monitored in closed PS II centers and its rise kinetics of approximately 25 nanoseconds is attributed to energy transfer from chlorophyll triplets in the antenna [see, Schlodder E and Brettel K (1988) Primary charge separation in closed photosystem II with a lifetime of 11 nanoseconds. Flash-absorption spectroscopy with oxygen-evolving photosystem II complexes from Synechococcus. Biochim Biophys Acta 933: 22–34]. It is conceivable that this process, that has a lower yield compared to the yield of radical-pair formation, plays a role in protecting chlorophyll from damage due to over-excitation.

The protective role of carotenoids in vivo has been elucidated through the use of bleaching herbicides such as norflurazon that inhibit carotenoid biosynthesis in all organisms performing oxygenic photosynthesis [reviewed by Sandmann G and Boger P (1989) Inhibition of carotenoid biosynthesis by herbicides. In: Boger P and Sandmann G (Eds.) Target Sites of Herbicide Action, pp 25–44. CRC Press, Boca Raton, Fla.]. Treatment with norflurazon in the light results in a decrease of both carotenoid and chlorophyll levels, while in the dark, chlorophyll levels are unaffected. Inhibition of photosynthetic efficiency in cells of *Oscillatoria agardhii* that were treated with the pyridinone herbicide, fluridone, was attributed to a decrease in the relative abundance of myxoxanthophyll, zeaxanthin and β-carotene, which in turn caused photooxidation of chlorophyll molecules [see, Canto de Loura I, Dubacq J P and Thomas J C (1987) The effects of nitrogen deficiency on pigments and lipids of cianobacteria. Plant Physiol 83: 838–843].

It has been demonstrated in plants that zeaxanthin is required to dissipate, in a nonradiative manner, the excess excitation energy of the antenna chlorophyll [see, Demmig-Adams B (1990) Carotenoids and photoprotection in plants: a role for the xanthophyll zeaxanthin. Biochim Biophys Acta 1020: 1–24; and, Demmig-Adams B and Adams W W III (1990) The carotenoid zeaxanthin and high-energy-state quenching of chlorophyll fluorescence. Photosynth Res 25: 187–197]. In algae and plants a light-induced deepoxidation of violaxanthin to yield zeaxanthin, is related to photoprotection processes [reviewed by Demmig-Adams B and Adams W W III (1992) Photoprotection and other responses of plants to high light stress. Ann Rev Plant Physiol Plant Mol Biol 43: 599–626]. The light-induced deepoxidation of violaxanthin and the reverse reaction that takes place in the dark, are known as the "xanthophyll cycle" [see, Demmig-Adams B and Adams W W III (1992) Photoprotection and other responses of plants to high light stress. Ann Rev Plant Physiol Plant Mol Biol 43: 599–626]. Cyanobacterial lichens, that do not contain any zeaxanthin and that probably are incapable of radiationless energy dissipation, are sensitive to high light intensity; algal lichens that contain zeaxanthin are more resistant to high-light stress [see, Demmig-Adams B, Adams W W III, Green T G A, Czygan F C and Lange O L (1990) Differences in the susceptibility to light stress in two lichens forming a phycosymbiodeme, one partner possessing and one lacking the xanthophyll cycle. Oecologia 84: 451–456; Demmig-Adams B and Adams W W III (1993) The xanthophyll cycle, protein turnover, and the high light tolerance of sun-acclimated leaves. Plant Physiol 103: 1413–1420; and, Demmig-Adams B (1990) Carotenoids and photoprotection in plants: a role for the xanthophyll zeaxanthin. Biochim Biophys Acta 1020: 1–24]. In contrast to algae and plants, cyanobacteria do not have a xanthophyll cycle. However, they do contain ample quantities of zeaxanthin and other xanthophylls that can support photoprotection of chlorophyll.

Several other functions have been ascribed to carotenoids. The possibility that carotenoids protect against damaging species generated by near ultra-violet (UV) irradiation is suggested by results describing the accumulation of β-carotene in a UV-resistant mutant of the cyanobacterium *Gloeocapsa alpicola* [see, Buckley C E and Houghton J A (1976) A study of the effects of near UV radiation on the pigmentation of the blue-green alga *Gloeocapsa alpicola*. Arch Microbiol 107: 93–97]. This has been demonstrated more elegantly in *Escherichia coli* cells that produce carotenoids [see, Tuveson R W and Sandmann G (1993) Protection by cloned carotenoid genes expressed in *Escherichia coli* against phototoxic molecules activated by near-ultraviolet light. Meth Enzymol 214: 323–330]. Due to their ability to quench oxygen radical species, carotenoids are efficient anti-oxidants and thereby protect cells from oxidative damage. This function of carotenoids is important in virtually all organisms [see, Krinsky N I (1989) Antioxidant functions of carotenoids. Free Radical Biol Med 7: 617–635; and, Palozza P and Krinsky N I (1992) Antioxidant effects of carotenoids in vivo and in vitro—an overview. Meth Enzymol 213: 403–420]. Other cellular functions could be affected by carotenoids, even if indirectly. Although carotenoids in cyanobacteria are not the major photoreceptors for phototaxis, an influence of carotenoids on phototactic reactions, that have been observed in *Anabaena variabilis*, was attributed to the removal of singlet oxygen radicals that may act as signal intermediates in this system [see, Nultsch W and Schuchart H (1985) A model of the phototactic reaction chain of cyanobacterium *Anabaena variabilis*. Arch Microbiol 142: 180–184].

In flowers and fruits carotenoids facilitate the attraction of pollinators and dispersal of seeds. This latter aspect is strongly associated with agriculture. The type and degree of pigmentation in fruits and flowers are among the most important traits of many crops. This is mainly since the colors of these products often determine their appeal to the consumers and thus can increase their market worth.

Carotenoids have important commercial uses as coloring agents in the food industry since they are non-toxic [see, Bauernfeind J C (1981) Carotenoids as colorants and vitamin A precursors. Academic Press, London]. The red color of the tomato fruit is provided by lycopene which accumulates during fruit ripening in chromoplasts. Tomato extracts, which contain high content (over 80% dry weight) of lycopene, are commercially produced worldwide for industrial use as food colorant. Furthermore, the flesh, feathers or eggs of fish and birds assume the color of the dietary carotenoid provided, and thus carotenoids are frequently used in dietary additives for poultry and in aquaculture. Certain cyanobacterial species, for example Spirulina sp. [see, Sommer T R, Potts W T and Morrissy N M (1990) Recent progress in processed microalgae in aquaculture. Hydrobiologia 204/205: 435–443], are cultivated in aquaculture for the production of animal and human food supplements. Consequently, the content of carotenoids, primarily of β-carotene, in these cyanobacteria has a major commercial implication in biotechnology.

Most carotenoids are composed of a $C_{40}$ hydrocarbon backbone, constructed from eight $C_5$ isoprenoid units and contain a series of conjugated double bonds. Carotenes do not contain oxygen atoms and are either linear or cyclized molecules containing one or two end rings. Xanthophylls are oxygenated derivatives of carotenes. Various glycosilated carotenoids and carotenoid esters have been identified. The $C_{40}$ backbone can be further extended to give $C_{45}$ or $C_{50}$ carotenoids, or shortened yielding apocarotenoids. Some nonphotosynthetic bacteria also synthesize $C_{30}$ carotenoids. General background on carotenoids can be found in Goodwin T W (1980) The Biochemistry of the Carotenoids, Vol. 1, 2nd Ed. Chapman and Hall, New York; and in Goodwin T W and Britton G (1988) Distribution and analysis of carotenoids. In: Goodwin T W (ed) Plant Pigments, pp 62–132. Academic Press, New York.

More than 640 different naturally-occurring carotenoids have been so far characterized, hence, carotenoids are responsible for most of the various shades of yellow, orange and red found in microorganisms, fungi, algae, plants and animals. Carotenoids are synthesized by all photosynthetic organisms as well as several nonphotosynthetic bacteria and fungi, however they are also widely distributed through feeding throughout the animal kingdom.

Carotenoids are synthesized de novo from isoprenoid precursors only in photosynthetic organisms and some microorganisms, they typically accumulate in protein complexes in the photosynthetic membrane, in the cell membrane and in the cell wall.

As detailed in FIG. 1, in the biosynthesis pathway of β-carotene, four enzymes convert geranylgeranyl pyrophosphate of the central isoprenoid pathway to β-carotene. Carotenoids are produced from the general isoprenoid biosynthetic pathway. While this pathway has been known for several decades, only recently, and mainly through the use of genetics and molecular biology, have some of the molecular mechanisms involved in carotenoids biogenesis, been elucidated. This is due to the fact that most of the enzymes which take part in the conversion of phytoene to carotenes and xanthophylls are labile, membrane-associated proteins that lose activity upon solubilization [see, Beyer P, Weiss G and Kleinig H (1985) Solubilization and reconstitution of the membrane-bound carotenogenic enzymes from daffodile chromoplasts. Eur J Biochem 153: 341–346; and, Bramley P M (1985) The in vitro biosynthesis of carotenoids. Adv Lipid Res 21: 243–279]. However, solubilization of carotenogenic enzymes from Synechocystis sp. strain PCC 6714 that retain partial activity has been reported [see, Bramley P M and Sandmann G (1987) Solubilization of carotenogenic enzyme of Aphanocapsa. Phytochem 26: 1935–1939]. There is no genuine in vitro system for carotenoid biosynthesis which enables a direct essay of enzymatic activities. A cell-free carotenogenic system has been developed [see, Clarke I E, Sandmann G, Bramley P M and Boger P (1982) Carotene biosynthesis with isolated photosynthetic membranes. FEBS Lett 140: 203–206] and adapted for cyanobacteria [see, Sandmann G and Bramley P M (1985) Carotenoid biosynthesis by Aphanocapsa homogenates coupled to a phytoene-generating system from *Phycomyces blakesleeanus*. Planta 164: 259–263; and, Bramley P M and Sandmann G (1985) In vitro and in vivo biosynthesis of xanthophylls by the cyanobacterium Aphanocapsa. Phytochem 24: 2919–2922]. Reconstitution of phytoene desaturase from Synechococcus sp. strain PCC 7942 in liposomes was achieved following purification of the polypeptide, that had been expressed in *Escherichia coli* [see, Fraser P D, Linden H and Sandmann G (1993) Purification and reactivation of recombinant Synechococcus phytoene desaturase from an overexpressing strain of *Escherichia coli*. Biochem J 291: 687–692].

Referring now to FIG. 1, carotenoids are synthesized from isoprenoid precursors. The central pathway of isoprenoid biosynthesis may be viewed as beginning with the conversion of acetyl-CoA to mevalonic acid. $D^3$-isopentenyl pyrophosphate (IPP), a $C_5$ molecule, is formed from mevalonate and is the building block for all long-chain isoprenoids. Following isomerization of IPP to dimethylallyl pyrophosphate (DMAPP), three additional molecules of IPP are combined to yield the $C_{20}$ molecule, geranylgeranyl pyrophosphate (GGPP). These 1'–4 condensation reactions are catalyzed by prenyl transferases [see, Kleinig H (1989) The role of plastids in isoprenoid biosynthesis. Ann Rev Plant Physiol Plant Mol Biol 40: 39–59]. There is evidence in plants that the same enzyme, GGPP synthase, carries out all the reactions from DMAPP to GGPP [see, Dogbo O and Camara B (1987) Purification of isopentenyl pyrophosphate isomerase and geranylgeranyl pyrophosphate synthase from Capsicum chromoplasts by affinity chromatography. Biochim Biophys Acta 920: 140–148; and, Laferriere A and Beyer P (1991) Purification of geranylgeranyl diphosphate synthase from *Sinapis alba* etioplasts. Biochim Biophys Acta 216: 156–163].

The first step that is specific for carotenoid biosynthesis is the head-to-head condensation of two molecules of GGPP to produce prephytoene pyrophosphate (PPPP). Following removal of the pyrophosphate, GGPP is converted to 15-cis-phytoene, a colorless $C_{40}$ hydrocarbon molecule. This two-step reaction is catalyzed by the soluble enzyme, phytoene synthase, an enzyme encoded by a single gene (crtB), in both cyanobacteria and plants [see, Chamovitz D, Misawa N, Sandmann G and Hirschberg J (1992) Molecular cloning and expression in *Escherichia coli* of a cyanobacterial gene coding for phytoene synthase, a carotenoid biosynthesis enzyme. FEBS Lett 296: 305–310; Ray J A, Bird C R, Maunders M, Grierson D and Schuch W (1987) Sequence of pTOM5, a ripening related cDNA from tomato. Nucl Acids Res 15: 10587–10588; Camara B (1993) Plant phytoene synthase complex—component 3 enzymes, immunology, and biogenesis. Meth Enzymol 214: 352–365]. All the subsequent steps in the pathway occur in membranes. Four desaturation (dehydrogenation) reactions convert phytoene to lycopene via phytofluene, ζ-carotene, and neurosporene. Each desaturation increases the number of conjugated double bonds by two such that the number of conjugated double bonds increases from three in phytoene to eleven in lycopene.

Relatively little is known about the molecular mechanism of the enzymatic dehydrogenation of phytoene [see, Jones B L and Porter J W (1986) Biosynthesis of carotenes in higher plants. CRC Crit Rev Plant Sci 3: 295–324; and, Beyer P, Mayer M and Kleinig H (1989) Molecular oxygen and the state of geometric iosomerism of intermediates are essential in the carotene desaturation and cyclization reactions in daffodil chromoplasts. Eur J Biochem 184: 141–150]. It has been established that in cyanobacteria, algae and plants the first two desaturations, from 15-cis-phytoene to ζ-carotene, are catalyzed by a single membrane-bound enzyme, phytoene desaturase [see, Jones B L and Porter J W (1986) Biosynthesis of carotenes in higher plants. CRC Crit Rev Plant Sci 3: 295–324; and, Beyer P, Mayer M and Kleinig H (1989) Molecular oxygen and the state of geometric isomerism of intermediates are essential in the carotene desaturation and cyclization reactions in daffodil chromoplasts. Eur J Biochem 184: 141–150]. Since the ζ-carotene product is mostly in the all-trans configuration, a cis-trans isomerization is presumed at this desaturation step. The primary structure of the phytoene desaturase polypeptide in cyanobacteria is conserved (over 65% identical residues) with that of algae and plants [see, Pecker I, Chamovitz D, Linden H, Sandmann G and Hirschberg J (1992) A single polypeptide catalyzing the conversion of phytoene to ζ-carotene is transcriptionally regulated during tomato fruit ripening. Proc Natl Acad Sci USA 89: 4962–4966; Pecker I, Chamovitz D, Mann V, Sandmann G, Boger P and Hirschberg J (1993) Molecular characterization of carotenoid biosynthesis in plants: the phytoene desaturase gene in tomato. In: Murata N (ed) Research in Photosynthesis, Vol III, pp 11–18. Kluwer, Dordrectht]. Moreover, the same inhibitors block phytoene desaturase in the two systems [see, Sandmann G and Boger P (1989) Inhibition of carotenoid biosynthesis by herbicides. In: Boger P and Sandmann G (eds) Target Sites of Herbicide Action, pp 25–44. CRC Press, Boca Raton, Fla.]. Consequently, it is very likely that the enzymes catalyzing the desaturation of phytoene and phytofluene in cyanobacteria and plants have similar biochemical and molecular properties, that are distinct from those of phytoene desaturases in other microorganisms. One such a difference is that phytoene desaturases from *Rhodobacter capsulatus*, Erwinia sp. or fungi convert phytoene to neurosporene, lycopene, or 3,4-dehydrolycopene, respectively.

Desaturation of phytoene in daffodil chromoplasts [see, Beyer P, Mayer M and Kleinig H (1989) Molecular oxygen and the state of geometric iosomerism of intermediates are essential in the carotene desaturation and cyclization reactions in daffodil chromoplasts. Eur J Biochem 184: 141–150], as well as in a cell free system of Synechococcus sp. strain PCC 7942 [see, Sandmann G and Kowalczyk S (1989) In vitro carotenogenesis and characterization of the phytoene desaturase reaction in Anacystis. Biochem Biophys Res Com 163: 916–921], is dependent on molecular oxygen as a possible final electron acceptor, although oxygen is not directly involved in this reaction. A mechanism of dehydrogenase-electron transferase was supported in cyanobacteria over dehydrogenation mechanism of dehydrogenase-monooxygenase [see, Sandmann G and Kowalczyk S (1989) In vitro carotenogenesis and characterization of the phytoene desaturase reaction in Anacystis. Biochem Biophys Res Com 163: 916–921]. A conserved FAD-binding motif exists in all phytoene desaturases whose primary structures have been analyzed [see, Pecker I, Chamovitz D, Linden H, Sandmann G and Hirschberg J (1992) A single polypeptide catalyzing the conversion of phytoene to ζ-carotene is transcriptionally regulated during tomato fruit ripening. Proc Natl Acad Sci USA 89: 4962–4966; Pecker I, Chamovitz D, Mann V, Sandmann G, Boger P and Hirschberg J (1993) Molecular characterization of carotenoid biosynthesis in plants: the phytoene desaturase gene in tomato. In: Murata N (ed) Research in Photosynthesis, Vol III, pp 11–18. Kluwer, Dordrectht]. The phytoene desaturase enzyme in pepper was shown to contain a protein-bound FAD [see, Hugueney P, Romer S, Kuntz M and Camara B (1992) Characterization and molecular cloning of a flavoprotein catalyzing the synthesis of phytofluene and ζ-carotene in Capsicum chromoplasts. Eur J Biochem 209: 399–407]. Since phytoene desaturase is located in the membrane, an additional, soluble redox component is predicted. This hypothetical component could employ NAD (P)$^+$, as suggested [see, Mayer M P, Nievelstein V and Beyer P (1992) Purification and characterization of a NADPH dependent oxidoreductase from chromoplasts of *Narcissus pseudonarcissus*—a redox-mediator possibly involved in carotene desaturation. Plant Physiol Biochem 30: 389–398] or another electron and hydrogen carrier, such as a quinone. The cellular location of phytoene desaturase in Synechocystis sp. strain PCC 6714 and *Anabaena variabilis* strain ATCC 29413 was determined with specific antibodies to be mainly (85%) in the photosynthetic thylakoid membranes [see, Serrano A, Gimenez P, Schmidt A and Sandmann G (1990) Immunocytochemical localization and functional determination of phytoene desaturase in photoautotrophic prokaryotes. J Gen Microbiol 136: 2465–2469].

In cyanobacteria algae and plants ζ-carotene is converted to lycopene via neurosporene. Very little is known about the enzymatic mechanism, which is predicted to be carried out by a single enzyme [see, Linden H, Vioque A and Sandmann G (1993) Isolation of a carotenoid biosynthesis gene coding for ζ-carotene desaturase from Anabaena PCC 7120 by heterologous complementation. FEMS Microbiol Lett 106: 99–104]. The deduced amino acid sequence of ζ-carotene desaturase in Anabaena sp. strain PCC 7120 contains a dinucleotide-binding motif that is similar to the one found in phytoene desaturase.

Two cyclization reactions convert lycopene to β-carotene. Evidence has been obtained that in Synechococcus sp. strain PCC 7942 [see, Cunningham F X Jr, Chamovitz D, Misawa N, Gantt E and Hirschberg J (1993) Cloning and functional expression in *Escherichia coli* of a cyanobacterial gene for lycopene cyclase, the enzyme that catalyzes the biosynthesis of β-carotene. FEBS Lett 328: 130–138], as well as in plants [see, Camara B and Dogbo O (1986) Demonstration and solubilization of lycopene cyclase from Capsicum chromoplast membranes. Plant Physiol 80: 172–184], these two cyclizations are catalyzed by a single enzyme, lycopene cyclase. This membrane-bound enzyme is inhibited by the triethylamine compounds, CPTA and MPTA [see, Sandmann G and Boger P (1989) Inhibition of carotenoid biosynthesis by herbicides. In: Boger P and Sandmann G (eds) Target Sites of Herbicide Action, pp 25–44. CRC Press, Boca Raton, Fla.]. Cyanobacteria carry out only the β-cyclization and therefore do not contain ε-carotene, δ-carotene and α-carotene and their oxygenated derivatives. The β-ring is formed through the formation of a "carbonium ion" intermediate when the C-1,2 double bond at the end of the linear lycopene molecule is folded into the position of the C-5,6 double bond, followed by a loss of a proton from C-6. No cyclic carotene has been reported in which the 7,8 bond is not a double bond. Therefore, full desaturation as in lycopene, or desaturation of at least half-molecule as in neurosporene, is essential for the reaction. Cyclization of lycopene involves a dehydrogenation reaction that does not require oxygen. The cofactor for this reaction is unknown. A dinucleotide-binding domain was found in the lycopene cyclase polypeptide of Synechococcus sp. strain PCC 7942, implicating NAD(P) or FAD as coenzymes with lycopene cyclase.

The addition of various oxygen-containing side groups, such as hydroxy-, methoxy-, oxo-, epoxy-, aldehyde or carboxylic acid moieties, form the various xanthophyll species. Little is known about the formation of xanthophylls. Hydroxylation of β-carotene requires molecular oxygen in a mixed-function oxidase reaction.

Clusters of genes encoding the enzymes for the entire pathway have been cloned from the purple photosynthetic bacterium *Rhodobacter capsulatus* [see, Armstrong G A, Alberti M, Leach F and Hearst J E (1989) Nucleotide sequence, organization, and nature of the protein products of the carotenoid biosynthesis gene cluster of *Rhodobacter capsulatus*. Mol Gen Genet 216: 254–268] and from the nonphotosynthetic bacteria *Erwinia herbicola* [see, Sandmann G, Woods W S and Tuveson R W (1990) Identification of carotenoids in *Erwinia herbicola* and in transformed *Escherichia coli* strain. FEMS Microbiol Lett 71: 77–82; Hundle B S, Beyer P, Kleinig H, Englert H and Hearst J E (1991) Carotenoids of *Erwinia herbicola* and an *Escherichia coli* HB101 strain carrying the *Erwinia herbicola* carotenoid gene cluster. Photochem Photobiol 54: 89–93; and, Schnurr G, Schmidt A and Sandmann G (1991) Mapping of a carotenogenic gene cluster from *Erwinia herbicola* and functional identification of six genes. FEMS Microbiol Lett 78: 157–162] and *Erwinia uredovora* [see, Misawa N, Nakagawa M, Kobayashi K, Yamano S, Izawa I, Nakamura K and Harashima K (1990) Elucidation of the *Erwinia uredovora* carotenoid biosynthetic pathway by functional analysis of gene products in *Escherichia coli*. J Bacteriol 172: 6704–6712]. Two genes, al-3 for GGPP synthase [see, Nelson M A, Morelli G, Carattoli A, Romano N and Macino G (1989) Molecular cloning of a *Neurospora crassa* carotenoid biosynthetic gene (albino-3) regulated by blue light and the products of the white collar genes. Mol Cell Biol 9: 1271–1276; and, Carattoli A, Romano N, Ballario P, Morelli G and Macino G (1991) The *Neurospora crassa* carotenoid biosynthetic gene (albino 3). J Biol Chem 266: 5854–5859] and al-1 for phytoene desaturase [see, Schmidhauser T J, Lauter F R, Russo V E A and Yanofsky C (1990) Cloning sequencing and photoregulation of al-1, a carotenoid biosynthetic gene of *Neurospora crassa*. Mol Cell Biol 10: 5064–5070] have been cloned from the fungus *Neurospora crassa*. However, attempts at using these genes as heterologous molecular probes to clone the corresponding genes from cyanobacteria or plants were unsuccessful due to lack of sufficient sequence similarity.

The first "plant-type" genes for carotenoid synthesis enzyme were cloned from cyanobacteria using a molecular-genetics approach. In the first step towards cloning the gene for phytoene desaturase, a number of mutants that are resistant to the phytoene-desaturase-specific inhibitor, norflurazon, were isolated in Synechococcus sp. strain PCC 7942 [see, Linden H, Sandmann G, Chamovitz D, Hirschberg J and Boger P (1990) Biochemical characterization of Synechococcus mutants selected against the bleaching herbicide norflurazon. Pestic Biochem Physiol 36: 46–51]. The gene conferring norflurazon-resistance was then cloned by transforming the wild-type strain to herbicide resistance [see, Chamovitz D, Pecker I and Hirschberg J (1991) The molecular basis of resistance to the herbicide norflurazon. Plant Mol Biol 16: 967–974; Chamovitz D, Pecker I, Sandmann G, Boger P and Hirschberg J (1990) Cloning a gene for norflurazon resistance in cyanobacteria. Z Naturforsch 45c: 482–486]. Several lines of evidence indicated that the cloned gene, formerly called pds and now named crtP, codes for phytoene desaturase. The most definitive one was the functional expression of phytoene desaturase activity in transformed *Escherichia coli* cells [see, Linden H, Misawa N, Chamovitz D, Pecker I, Hirschberg J and Sandmann G (1991) Functional complementation in *Escherichia coli* of different phytoene desaturase genes and analysis of accumulated carotenes. Z Naturforsch 46c: 1045–1051; and, Pecker I, Chamovitz D, Linden H, Sandmann G and Hirschberg J (1992) A single polypeptide catalyzing the conversion of phytoene to ζ-carotene is transcriptionally regulated during tomato fruit ripening. Proc Natl Acad Sci USA 89: 4962–4966]. The crtP gene was also cloned from Synechocystis sp. strain PCC 6803 by similar methods [see, Martinez-Ferez I M and Vioque A (1992) Nucleotide sequence of the phytoene desaturase gene from Synechocystis sp. PCC 6803 and characterization of a new mutation which confers resistance to the herbicide norflurazon. Plant Mol Biol 18: 981–983].

The cyanobacterial crtP gene was subsequently used as a molecular probe for cloning the homologous gene from an alga [see, Pecker I, Chamovitz D, Mann V, Sandmann G, Boger P and Hirschberg J (1993) Molecular characterization of carotenoid biosynthesis in plants: the phytoene desaturase gene in tomato. In: Murata N (ed) Research in Photosynthesis, Vol III, pp 11–18. Kluwer, Dordrectht] and higher plants [see, Bartley G E, Viitanen P V, Pecker I, Chamovitz D, Hirschberg J and Scolnik P A (1991) Molecular cloning and expression in photosynthetic bacteria of a soybean cDNA coding for phytoene desaturase, an enzyme of the carotenoid biosynthesis pathway. Proc Natl Acad Sci USA 88: 6532–6536; and, Pecker I, Chamovitz D, Linden H, Sandmann G and Hirschberg J (1992) A single polypeptide catalyzing the conversion of phytoene to ζ-carotene is transcriptionally regulated during tomato fruit ripening. Proc Natl Acad Sci USA 89: 4962–4966]. The phytoene desaturases in Synechococcus sp. strain PCC 7942 and Synechocystis sp. strain PCC 6803 consist of 474 and 467 amino acid residues, respectively, whose sequences are highly conserved (74% identities and 86% similarities). The calculated molecular mass is 51 kDa and, although it is slightly hydrophobic (hydropathy index -0.2), it does not include a hydrophobic region which is long enough to span a lipid bilayer membrane. The primary structure of the cyanobacterial phytoene desaturase is highly conserved with the enzyme from the green alga *Dunalliela bardawil* (61% identical and 81% similar; [see, Pecker I, Chamovitz D, Mann V, Sandmann G, Boger P and Hirschberg J (1993) Molecular characterization of carotenoid biosynthesis in plants: the phytoene desaturase gene in tomato. In: Murata N (ed) Research in Photosynthesis, Vol III, pp 11–18. Kluwer, Dordrectht]) and from tomato [see, Pecker I, Chamovitz D, Linden H, Sandmann G and Hirschberg J (1992) A single polypeptide catalyzing the conversion of phytoene to ζ-carotene is transcriptionally regulated during tomato fruit ripening. Proc Natl Acad Sci USA 89: 4962–4966], pepper [see, Hugueney P, Romer S, Kuntz M and Camara B (1992) Characterization and molecular cloning of a flavoprotein catalyzing the synthesis of phytofluene and ζ-carotene in Capsicum chromoplasts. Eur J Biochem 209: 399–407] and soybean [see, Bartley G E, Viitanen P V, Pecker I, Chamovitz D, Hirschberg J and Scolnik P A (1991) Molecular cloning and expression in photosynthetic bacteria of a soybean cDNA coding for phytoene desaturase, an enzyme of the carotenoid biosynthesis pathway. Proc Natl Acad Sci USA 88: 6532–6536] (62–65% identical and ~79% similar; [see, Chamovitz D (1993) Molecular analysis of the early steps of carotenoid biosynthesis in cyanobacteria: Phytoene synthase and phytoene desaturase. Ph.D. Thesis, The Hebrew University of Jerusalem]). The eukaryotic phytoene desaturase polypeptides are larger (64 kDa); however, they are processed during import into the plastids to mature forms whose sizes are comparable to those of the cyanobacterial enzymes.

There is a high degree of structural similarity in carotenoid enzymes of *Rhodobacter capsulatus*, Erwinia sp. and *Neurospora crassa* [reviewed in Armstrong G A, Hundle B S and Hearst J E (1993) Evolutionary conservation and structural similarities of carotenoid biosynthesis gene products from photosynthetic and nonphotosynthetic organisms. Meth Enzymol 214: 297–311], including in the crtI gene-product, phytoene desaturase. As indicated above, a high degree of conservation of the primary structure of phytoene desaturases also exists among oxygenic photosynthetic organisms. However, there is little sequence similarity, except for the FAD binding sequences at the amino termini, between the "plant-type" crtP gene products and the "bacterial-type" phytoene desaturases (crtI gene products; 19–23% identities and 42–47% similarities). It has been hypothesized that crtP and crtI are not derived from the same ancestral gene and that they originated independently through convergent evolution [see, Pecker I, Chamovitz D, Linden H, Sandmann G and Hirschberg J (1992) A single polypeptide catalyzing the conversion of phytoene to ζ-carotene is transcriptionally regulated during tomato fruit ripening. Proc Natl Acad Sci USA 89: 4962–4966]. This hypothesis is supported by the different dehydrogenation sequences that are catalyzed by the two types of enzymes and by their different sensitivities to inhibitors.

Although not as definite as in the case of phytoene desaturase, a similar distinction between cyanobacteria and plants on the one hand and other microorganisms is also seen in the structure of phytoene synthase. The crtB gene (formerly psy) encoding phytoene synthase was identified in the genome of Synechococcus sp. strain PCC 7942 adjacent to crtP and within the same operon [see, Bartley G E, Viitanen P V, Pecker I, Chamovitz D, Hirschberg J and Scolnik P A (1991) Molecular cloning and expression in photosynthetic bacteria of a soybean cDNA coding for phytoene desaturase, an enzyme of the carotenoid biosynthesis pathway. Proc Natl Acad Sci USA 88: 6532–6536]. This gene encodes a 36-kDa polypeptide of 307 amino acids with a hydrophobic index of −0.4. The deduced amino acid sequence of the cyanobacterial phytoene synthase is highly conserved with the tomato phytoene synthase (57% identical and 70% similar; Ray J A, Bird C R, Maunders M, Grierson D and Schuch W (1987) Sequence of pTOM5, a ripening related cDNA from tomato. Nucl Acids Res 15: 10587–10588]) but is less highly conserved with the crtB sequences from other bacteria (29–32% identical and 48–50% similar with ten gaps in the alignment). Both types of enzymes contain two conserved sequence motifs also found in prenyl transferases from diverse organisms [see, Bartley G E, Viitanen P V, Pecker I, Chamovitz D, Hirschberg J and Scolnik P A (1991) Molecular cloning and expression in photosynthetic bacteria of a soybean cDNA coding for phytoene desaturase, an enzyme of the carotenoid biosynthesis pathway. Proc Natl Acad Sci USA 88: 6532–6536; Carattoli A, Romano N, Ballario P, Morelli G and Macino G (1991) The *Neurospora crassa* carotenoid biosynthetic gene (albino 3). J Biol Chem 266: 5854–5859; Armstrong G A, Hundle B S and Hearst J E (1993) Evolutionary conservation and structural similarities of carotenoid biosynthesis gene products from photosynthetic and nonphotosynthetic organisms. Meth Enzymol 214: 297–311; Math S K, Hearst J E and Poulter C D (1992) The crtE gene in *Erwinia herbicola* encodes geranylgeranyl diphosphate synthase. Proc Natl Acad Sci USA 89: 6761–6764; and, Chamovitz D (1993) Molecular analysis of the early steps of carotenoid biosynthesis in cyanobacteria: Phytoene synthase and phytoene desaturase. Ph.D. Thesis, The Hebrew University of Jerusalem]. It is conceivable that these regions in the polypeptide are involved in the binding and/or removal of the pyrophosphate during the condensation of two GGPP molecules.

The crtQ gene encoding ζ-carotene desaturase (formerly zds) was cloned from Anabaena sp. strain PCC 7120 by screening an expression library of cyanobacterial genomic DNA in cells of *Escherichia coli* carrying the Erwinia sp. crtB and crtE genes and the cyanobacterial crtP gene [see, Linden H, Vioque A and Sandmann G (1993) Isolation of a carotenoid biosynthesis gene coding for ζ-carotene desaturase from Anabaena PCC 7120 by heterologous complementation. FEMS Microbiol Lett 106: 99–104]. Since these *Escherichia coli* cells produce ζ-carotene, brownish-red pigmented colonies that produced lycopene could be identified on the yellowish background of cells producing ζ-carotene. The predicted ζ-carotene desaturase from Anabaena sp. strain PCC 7120 is a 56-kDa polypeptide which consists of 499 amino acid residues. Surprisingly, its primary structure is not conserved with the "plant-type" (crtP gene product) phytoene desaturases, but it has considerable sequence similarity to the bacterial-type enzyme (crtI gene product) [see, Sandmann G (1993) Genes and enzymes involved in the desaturation reactions from phytoene to lycopene. (abstract), 10th International Symposium on Carotenoids, Trondheim CL1-2]. It is possible that the cyanobacterial crtQ gene and crtI gene of other microorganisms originated in evolution from a common ancestor.

The crtL gene for lycopene cyclase (formerly lcy) was cloned from Synechococcus sp. strain PCC 7942 utilizing essentially the same cloning strategy as for crtP. By using an inhibitor of lycopene cyclase, 2-(4-methylphenoxy)-triethylamine hydrochloride (MPTA), the gene was isolated by transformation of the wild-type to herbicide-resistance [see, Cunningham F X Jr, Chamovitz D, Misawa N, Gantt E and Hirschberg J (1993) Cloning and functional expression in *Escherichia coli* of a cyanobacterial gene for lycopene cyclase, the enzyme that catalyzes the biosynthesis of β-carotene. FEBS Lett 328: 130–138]. Lycopene cyclase is the product of a single gene product and catalyzes the double cyclization reaction of lycopene to β-carotene. The crtL gene product in Synechococcus sp. strain PCC 7942 is a 46-kDa polypeptide of 411 amino acid residues. It has no sequence similarity to the crtY gene product (lycopene cyclase) from *Erwinia uredovora* or *Erwinia herbicola*.

The gene for β-carotene hydroxylase (crtZ) and zeaxanthin glycosilase (crtX) have been cloned from *Erwinia herbicola* [see, Hundle B, Alberti M, Nievelstein V, Beyer P, Kleinig H, Armstrong G A, Burke D H and Hearst J E (1994) Functional assignment of *Erwinia herbicola* Eho10 carotenoid genes expressed in *Escherichia coli*. Mol Gen Genet 254: 406–416; Hundle B S, Obrien D A, Alberti M, Beyer P and Hearst J E (1992) Functional expression of zeaxanthin glucosyltransferase from *Erwinia herbicola* and a proposed diphosphate binding site. Proc Natl Acad Sci USA 89: 9321–9325] and from *Erwinia uredovora* [see, Misawa N, Nakagawa M, Kobayashi K, Yamano S, Izawa I, Nakamura K and Harashima K (1990) Elucidation of the *Erwinia uredovora* carotenoid biosynthetic pathway by functional analysis of gene products in *Escherichia coli*. J Bacteriol 172: 6704–6712].

The ketocarotenoid astaxanthin (3,3'-dihydroxy-β,β-carotene-4,4'-dione) was first described in aquatic crustaceans as an oxidized form of β-carotene. Astaxanthin was later found to be very common in many marine animals and algae. However, only few animals can synthesize astaxanthin de novo from other carotenoids and most of them obtain it in their food. In the plant kingdom, astaxanthin occurs mainly in some species of cyanobacteria, algae and lichens. However, it is found rarely also in petals of higher plant species [see, Goodwin T W (1980) The Biochemistry of the carotenoids, Vol. 1. 2nd Ed, Chapman and Hall, London and New York].

The function of astaxanthin as a powerful antioxidant in animals has been demonstrated [see, Miki W (1991) Biological functions and activities of animal carotenoids. Pure Appl Chem 63: 141]. Astaxanthin is a strong inhibitor of lipid peroxidation and has been shown to play an active role in the protection of biological membranes from oxidative injury [see, Palozza P and Krinsky N I (1992) Antioxidant effects of carotenoids in vivo and in vitro—an overview. Methods Enzymol 213: 403–420; and, Kurashige M, Okimasu E, Inove M and Utsumi K (1990) Inhibition of oxidative injury of biological membranes by astaxanthin. Physiol Chem Phys Med NMR 22: 27]. The chemopreventive effects of astaxanthin have also been investigated in which astaxanthin was shown to significantly reduce the incidence of induced urinary bladder cancer in mice [see, Tanaka T, Morishita Y, Suzui M, Kojima T, Okumura A. and Mori H (1994). Chemoprevention of mouse urinary bladder carcinogenesis by the naturally occurring carotenoid astaxanthin. Carcinogenesis 15: 15]. It has also been demonstrated that astaxanthin exerts immunomodulating effects by enhancing antibody production [see, Jyonouchi H, Zhang L and Tomita Y (1993) Studies of immunomodulating actions of carotenoids. II. Astaxanthin enhances in vitro antibody production to T-dependent antigens without facilitating polyclonal B-cell activation. Nutr Cancer 19: 269; and, Jyonouchi H, Hill J R, Yoshifumi T and Good R A (1991) Studies of immunomodulating actions of carotenoids. I. Effects of β-carotene and astaxanthin on murine lymphocyte functions and cell surface marker expression in-vitro culture system. Nutr Cancer 16: 93]. The complete biomedical properties of astaxanthin remain to be elucidated, but initial results suggest that it could play an important role in cancer and tumor prevention, as well as eliciting a positive response from the immune system.

Astaxanthin is the principal carotenoid pigment of salmonids and shrimps and imparts attractive pigmentation in the eggs, flesh and skin [see, Torrisen O J, Hardy R W, Shearer K D (1989) Pigmentation of salmonid-carotenoid deposition and metabolism in salmonids. Crit Rev Aquatic Sci 1: 209]. The world-wide harvest of salmon in 1991 was approximately 720,000 MT., of which 25–30% were produced in a variety of aquaculture facilities [see, Meyers S P (1994) Developments in world aquaculture, feed formulations, and role of carotenoids. Pure Appl Chem 66: 1069]. This is set to increase up to 460,000 MT. by the year 2000 [see, Bjorndahl T (1990) The Economics of Salmon Aquaculture. Blackwell Scientific, Oxford. pp. 1]. The red coloration of the salmonid flesh contributes to consumer appeal and therefore affects the price of the final product. Animals cannot synthesize carotenoids and they acquire the pigments through the food chain from the primary producers—marine algae and phytoplankton. Those grown in intensive culture usually suffer from suboptimal color. Consequently, carotenoid-containing nourishment is artificially added in aquaculture, at considerable cost to the producer.

Astaxanthin is the most expensive commercially used carotenoid compound (todays-1995 market value is of 2,500–3,500 $/kg). It is utilized mainly as nutritional supplement which provides pigmentation in a wide variety of aquatic animals. In the Far-East it is used also for feeding poultry to yield a typical pigmentation of chickens. It is also a desirable and effective nontoxic coloring for the food industry and is valuable in cosmetics. Recently it was reported that astaxanthin is a potent antioxidant in humans and thus is a desirable food additive.

Natural (3S,3'S) astaxanthin is limited in availability. It is commercially extracted from some crustacea species [see, Torrisen O J, Hardy R W, Shearer K D (1989) Pigmentation of salmonid-carotenoid deposition and metabolism in salmonids. Crit Rev Aquatic Sci 1: 209]. The (3R,3'R) stereoisomer of astaxanthin is produced from Phaffia [a yeast specie, see, Andrewes A G, Phaff H J and Starr M P (1976) Carotenoids of *Phaffia rhodozyma*, a red-pigmented fermenting yeast. Phytochemistry Vol. 15, pp. 1003–1007]. Synthetic astaxanthin, comprising a 1:2:1 mixture of the (3S,3'S)-, (3S,3'R)- and (3R,3'R)-isomers is now manufactured by Hoffman-La Roche and sold at a high price (ca. $2,500/Kg) under the name "CAROPHYLL Pink" [see, Mayer H (1994) Reflections on carotenoid synthesis. Pure & Appl Chem, Vol. 66, pp. 931–938]. Recently a novel gene involved in ketocompound biosynthesis, designated crtW was isolated from the marine bacteria *Agrobacterium auranticacum* and Alcaligenes PC-1 that produce ketocarotenoids such as astaxanthin. When the crtW gene was introduced into engineered *Eschrichia coli* that accumulated β-carotene due to Erwinia carotenogenic genes, the *Escherichia coli* transformants synthesized canthaxanthin a precursor in the synthetic pathway of astaxanthin [see, Misawa N, Kajiwara S, Kondo K, Yokoyama A, Satomi Y, Saito T, Miki W and Ohtani T (1995) Canthaxanthin biosynthesis by the conversion of methylene to keto groups in a hydrocarbon β-carotene by a single gene. Biochemical and biophysical research communications Vol. 209, pp. 867–876]. It is therefore desirable to find a relatively inexpensive source of (3S,3'S) astaxanthin to be used as a feed supplement in aquaculture and as a valuable chemical for various other industrial uses.

Although astaxanthin is synthesized in a variety of bacteria, fungi and algae, the key limitation to the use of biological systems for its production is the low yield of and costly extraction methods in these systems compared to chemical synthesis. One way to solve these problems is to increase the productivity of astaxanthin production in biological systems using recombinant DNA technology. This allows for the production of astaxanthin in genetically engineered host which, in the case of a higher plant, is easy to grow and simple to extract. Furthermore, production of astaxanthin in genetically engineered host enables by appropriate host selection to use thus produced astaxanthin in for example aquaculture applications, devoid of the need for extraction.

There is thus a widely recognized need for, and it would be highly advantageous to have, a nucleic acid segment which encodes β-C-4-oxygenase, the enzyme that converts β-carotene to canthaxanthin, as well as recombinant vector molecules comprising a nucleic acid sequence according to the invention, and host cells or transgenic organisms transformed or transfected with these vector molecules or DNA segment for the biotechnological production of (3S,3'S) astaxanthin.

SUMMARY OF THE INVENTION

It is a general object of this invention to provide a biotechnological method for production of (3S,3'S) astaxanthin.

It is a specific object of the invention to provide a peptide having a β-C-4-oxygenase activity and a DNA segment coding for this peptide to enable a biotechnological production of astaxanthin and other xanthophylls.

It is a further object of the invention to provide an RNA segments coding for a polypeptide comprising an amino acid sequence corresponding to above described peptide.

It is yet a further object of the invention to provide a recombinant DNA molecule comprising a vector and the DNA segment as described above.

It is still a further object of the invention to provide a host cell containing the above described recombinant DNA molecule.

It is another object of the invention to provide a host transgenic organism containing the above described recombinant DNA molecule or the above described DNA segment in its cells.

It is still another object of the invention to provide a host transgenic organism which expresses β-C-4-oxygenase activity in chloroplasts and/or chromoplasts-containing tissues.

It is yet another object of the invention to provide a food additive for animal or human consumption comprising the above described host cell or transgenic organism.

It is still another object of the invention to provide a method of producing astaxanthin using the above described host cell or transgenic organism.

It is a further object of the invention to provide a method of producing canthaxanthin, echinenone, cryptoxanthin, isocryptoxanthin hydroxyechinenone, zeaxanthin, adonirubin, and/or adonixanthin using the above described host cell or transgenic organism.

Further objects and advantages of the present invention will be clear from the description that follows.

In one embodiment, the present invention relates to a DNA segment coding for a polypeptide comprising an amino acid sequence corresponding to *Haematococcus pluvialis* crtO gene.

In a further embodiment, the present invention relates to an RNA segment coding for a polypeptide comprising an amino acid sequence corresponding to *Haematococcus pluvialis* crtO gene.

In yet another embodiment, the present invention relates to a polypeptide comprising an amino acid sequence corresponding to a *Haematococcus pluvialis* crtO gene.

In a further embodiment, the present invention relates to a recombinant DNA molecule comprising a vector and a DNA segment coding for a polypeptide, corresponding to a *Haematococcus pluvialis* crtO gene.

In another embodiment, the present invention relates to a host cell containing the above described recombinant DNA molecule or DNA segment.

In a further embodiment, the present invention relates to a host transgenic organism containing the above described recombinant DNA molecule or the above described DNA segment in its cells.

In another embodiment, the present invention relates to a method of producing astaxanthin using the above described host cell or transgenic organism.

In yet another embodiment, the present invention relates to a method of producing other xanthophylls.

In still another embodiment, the present invention relates to a method of obtaining high expression of a transgene in plants specifically in chromoplasts-containing cells.

In one further embodiment, the present invention relates to a method of importing a carotenoid-biosynthesis enzyme encoded by a transgene into chromoplasts.

BRIEF DESCRIPTION OF THE DRAWINGS

The invention herein described, by way of example only, with reference to the accompanying drawings, wherein:

FIG. 2 is an identity map between the nucleotide sequence of the crtO cDNA of the present invention (CRTOA.SEQ) and the cDNA cloned by Kajiwara et al., (CRTOJ.SEQ) [see, Kajiwara S, Kakizono T, Saito T, Kondo K, Ohtani T, Nishio N, Nagai S and Misawa N (1995) Isolation and functional identification of a novel cDNA for astaxanthin biosynthesis from *Haematococcus pluvialis*, and astaxanthin synthesis in *Escherichia coli*. Plant Molec Biol 29: 343–352], using a GCG software, wherein (:) indicate identity, (-) indicate a gap and nucleotides numbering is according to SEQ ID NO:4 for CRTOA.AMI and Kajiwara et al., for CRTO-J.AMI;

FIG. 3 is an identity map between the amino acid sequence encoded by the crtO cDNA of the present invention (CRTOA.AMI) and the amino acid sequence encoded by the cDNA cloned by Kajiwara et al., (CRTOJ.AMI) [see, Kajiwara S, Kakizono T. Saito T, Kondo K, Ohtani T, Nishio N, Nagai S and Misawa N (1995) Isolation and functional identification of a novel cDNA for astaxanthin biosynthesis from *Haematococcus pluvialis*, and astaxanthin synthesis in *Escherichia coli*. Plant Molec Biol 29: 343–352], using a GCG software, wherein (:) indicate identity, (-) indicate a gap and amino acids numbering is according to SEQ ID NO:4 for CRTOA.AMI and Kajiwara et al., for CRTO-J.AMI;

DESCRIPTION OF THE PREFERRED EMBODIMENTS

Figure 1:
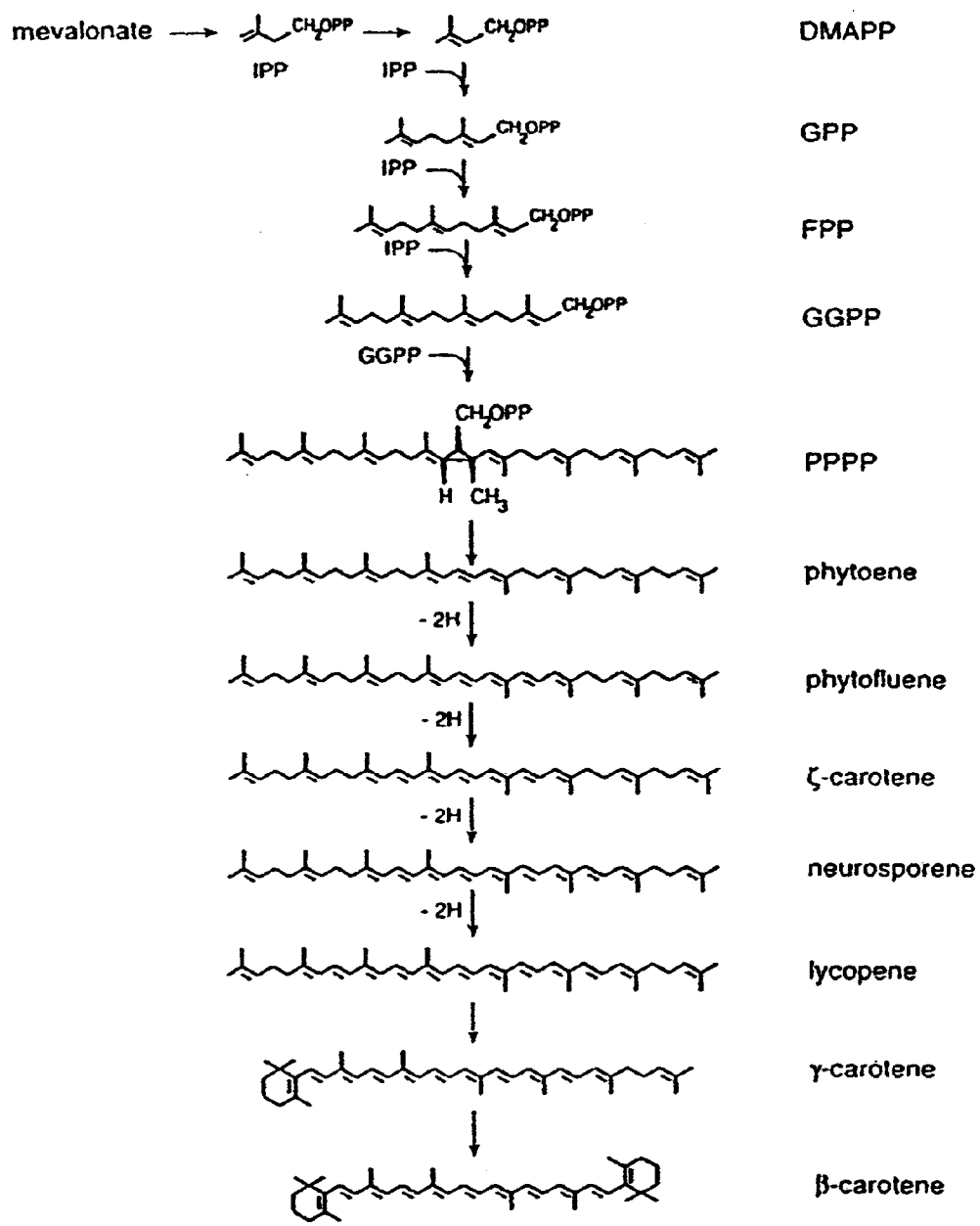
FIG. 1 is a general biochemical pathway of β-carotene biosynthesis, in which pathway all molecules are depicted in an all-trans configuration, wherein IPP is isopentenyl pyrophosphate, DMAPP is dimethylallyl pyrophosphate, GPP is geranyl pyrophosphate, FPP is farnesyl pyrophosphate, GGPP is geranylgeranyl pyrophosphate and, PPPP is prephytoene pyrophosphate.

The present invention is, in general, of a biotechnological method for production of (3S,3'S) astaxanthin. In particular, the present invention is of a peptide having a β-C-4-oxygenase activity; a DNA segment coding for this peptide; an RNA segments coding for this peptide; a recombinant DNA molecule comprising a vector and the DNA segment; a host cell or organism containing the above described recombinant DNA molecule or DNA segment; and of a method for biotechnologically producing (3S,3'S) astaxanthin or a food additive containing (3S,3'S) astaxanthin, using the host.

The unicellular fresh-water green alga *Haematococcus pluvialis* accumulates large amounts of (3S,3'S) astaxanthin when exposed to unfavorable growth conditions, or following different environmental stresses such as phosphate or nitrogen starvation, high concentration of salt in the growth medium or high light intensity [see, Yong Y Y R and Lee Y K (1991) Phycologia 30 257–261; Droop M R (1954) Arch Microbiol 20: 391–397; and, Andrewes A. G, Borch G, Liaaen-Jensen S and Snatzke G.(1974) Acta Chem Scand B28: 730–736]. During this process, the vegetative cells of the alga form cysts and change their color from green to red. The present invention discloses the cloning of a cDNA from *Haematococcus pluvialis*, designated crtO, which encodes a β-C-4-oxygenase, the enzyme that converts β-carotene to canthaxanthin, and its expression in a heterologous systems expressing β-carotene hydroxylase (e.g., *Erwinia herbicola* crtZ gene product), leading to the production of (3S,3'S) astaxanthin.

The crtO cDNA and its encoded peptide having a β-C-4-oxygenase activity are novel nucleic and amino acid sequences, respectively. The cloning method of the crtO cDNA took advantage of a strain of *Escherichia coli*, which was genetically engineered to produce β-carotene, to which a cDNA library of *Haematococcus pluvialis* was transfected and expressed. Visual screening for brown-red pigmented *Escherichia coli* cells has identified a canthaxanthin producing transformant. Thus cloned cDNA has been expressed in two heterologous systems (*Escherichia coli* and Synechococcus PCC7942 cells) both able to produce β-carotene and further include an engineered (*Erwinia herbicola* crtZ gene product) or endogenous β-carotene hydroxylase activity, and was shown to enable the production of (3S,3'S) astaxanthin in both these systems.

The crtO cDNA or its protein product exhibit no meaningful nucleic- or amino acid sequence similarities to the nucleic- or amino acid sequence of crtW and its protein product isolated from the marine bacteria *Agrobacterium auranticacum* and Alcaligenes PC-1 that produce ketocarotenoids such as astaxanthin [see, Misawa N, Kajiwara S, Kondo K, Yokoyama A, Satomi Y, Saito T, Miki W and Ohtani T (1995) Canthaxanthin biosynthesis by the conversion of methylene to keto groups in a hydrocarbon β-carotene by a single gene. Biochemical and biophysical research communications Vol. 209, pp. 867–876].

Figure 2:
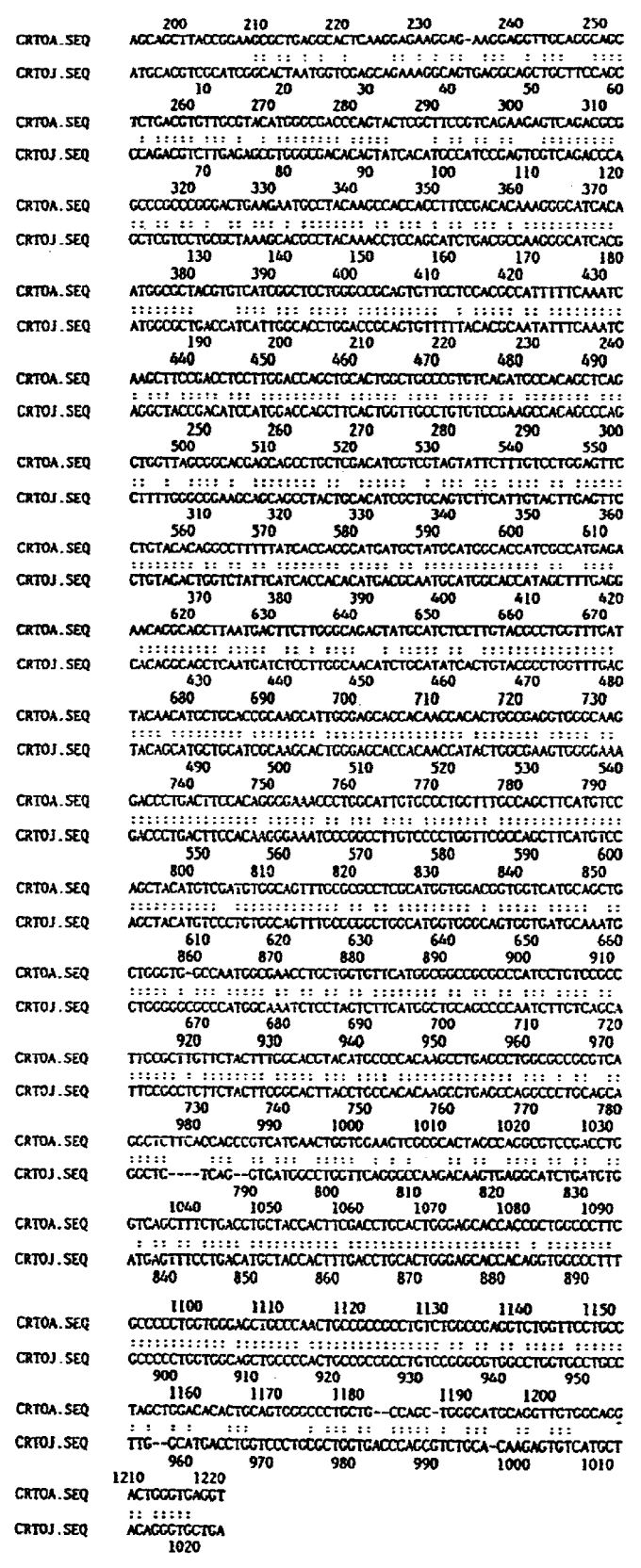

However, the crtO cDNA and its protein product exhibit substantial nucleic- and amino acid sequence identities with the nucleic- and amino acid sequence of a recently cloned cDNA encoding a 320 amino acids protein product having β-carotene oxygenase activity, isolated from *Haematococcus pluvialis* [see, Kajiwara S, Kakizono T, Saito T, Kondo K, Ohtani T, Nishio N, Nagai S and Misawa N (1995) Isolation and functional identification of a novel cDNA for astaxanthin biosynthesis from *Haematococcus pluvialis*, and astaxanthin synthesis in *Escherichia coli*. Plant Molec Biol 29: 343–352]. Nevertheless, as presented in FIG. 2 the degree of sequence identity between the crtO cDNA (CRTOA.SEQ in FIG. 2) and the cDNA described by Kajiwara et al. (CRTOJ.SEQ in FIG. 2) [see reference above] is 75.7% and, as presented in FIG. 3 the degree of sequence identity between the crtO cDNA protein product (CRTOA.AMI in FIG. 3) and the protein described by Kajiwara et al. (CRTOJ.AMI in FIG. 3) is 78%, as was determined using a GCG software.

As will be described in details hereinbelow, the crtO cDNA can thus be employed to biotechnologically produce (3S,3'S) astaxanthin in systems which are either easy to grow and can be used directly as an additive to fish food, or systems permitting a simple and low cost extraction procedure of astaxanthin.

In one embodiment, the present invention relates to a DNA segment coding for a polypeptide comprising an amino acid sequence corresponding to *Haematococcus pluvialis* crtO gene and allelic and species variations and functional naturally occurring and/or man-induced variants thereof. The phrase 'allelic and species variations and functional naturally occurring and/or man-induced variants' as used herein and in the claims below refer to the source of the DNA (or RNA as described below) or means known in the art for obtaining it. However the terms 'variation' and 'variants' indicate the presence of sequence dissimilarities (i.e., variations). It is the intention herein and in the claims below that the sequence variations will be 77–80%, preferably 80–85%, more preferably 85–90%, most preferably 90–100% of identical nucleotides. In a preferred embodiment the DNA segment comprises the sequence set forth in SEQ ID NO:1. In another preferred embodiment, the DNA segment encodes the amino acid sequence set forth in SEQ ID NO:4.

The invention also includes a pure DNA segment characterized as including a sequence which hybridizes under high stringency conditions [e.g., as described in Sambrook et al., Molecular Cloning; A Laboratory Manual. Cold Spring Harbor Laboratory, Cold Spring Harbor, N.Y. 1989] to a nucleic acid probe which includes at least fifteen, preferably at least fifty, more preferably at least hundred, even more preferably at least two hundred, even more preferably at least five hundred successive nucleotides of SEQ ID NO:1 or SEQ ID NO:2. Alternatively, the DNA segment of the invention may be characterized as being capable of hybridizing under low-stringent conditions to a nucleic acid probe which includes the coding sequence (nucleotides 166 through 1152) of SEQ ID NO:1 or SEQ ID NO:2. An example of such low-stringency conditions is as described in Sambrook et al., using a lower hybridization temperature, such as, for example, 20° C. below the temperature employed for high-stringency hybridization conditions, as described above.

The DNA segment of the invention may also be characterized as being capable of hybridizing under high-stringent conditions to a nucleic acid probe which includes the coding sequence (nucleotides 166 through 1152) of SEQ ID NO:1 or SEQ ID NO:2.

The invention also includes a synthetically produced oligonucleotide (e.g., oligodeoxyribonucleotide or oligoribonucleotide and analogs thereof) capable of hybridizing with at least ten-nucleotide segments of SEQ ID NO:1 or SEQ ID NO:2.

In another embodiment, the present invention relates to an RNA segment coding for a polypeptide comprising an amino acid sequence corresponding to *Haematococcus pluvialis* crtO gene and allelic and species variations and functional naturally occurring and/or man-induced variants thereof. In a preferred embodiment the RNA segment comprises the sequence set forth in SEQ ID NO:2. In another preferred embodiment, the RNA segment encodes the amino acid sequence set forth in SEQ ID NO:4.

The invention also includes a pure RNA characterized as including a sequence which hybridizes under high stringent conditions to a nucleic acid probe which includes at least at least fifteen, preferably at least fifty, more preferably at least hundred, even more preferably at least two hundred, even more preferably at least five hundred succsesive nucleotides of SEQ ID NO:1 or SEQ ID NO:2. Alternatively, the RNA of the invention may be characterized as being capable of hybridizing under low-stringent conditions to a nucleic acid probe which includes the coding sequence (nucleotides 166 through 1152) of SEQ ID NO:1 or SEQ ID NO:2. Additionally, the RNA of the invention may be characterized as being capable of hybridizing under high-stringent conditions to a nucleic acid probe which includes the coding sequence (nucleotides 166 through 1152) of SEQ ID NO:1 or SEQ ID NO:2.

In another embodiment, the present invention relates to a polypeptide comprising an amino acid sequence corresponding to a *Haematococcus pluvialis* crtO gene and allelic, species variations and functional naturally occurring and/or man-induced variants thereof. In a preferred embodiment, the polypeptide comprises the amino acid sequence set forth in SEQ ID NO:4.

It should be noted that the invention includes any peptide which is homologous (i.e., 80–85%, preferably 85–90%, more preferably 90–100% of identical amino acids) to the above described polypeptide. The term 'homologous' as used herein and in the claims below, refers to the sequence identity between two peptides. When a position in both of the two compared sequences is occupied by identical amino acid monomeric subunits, it is homologous at that position. The homology between two sequences is a function of the number of homologous positions shared by the two sequences. For example, if eight of ten of the positions in two sequences are occupied by identical amino acids then the two sequences are 80% homologous.

Other polypeptides which are also included in the present invention are allelic variations, other species homologs, natural mutants, induced mutants and peptides encoded by DNA that hybridizes under high or low stringency conditions (see above) to the coding region (nucleotides 166 through 1152) of SEQ ID NO:1 or SEQ ID NO:2.

In another embodiment, the present invention relates to a recombinant DNA molecule comprising a vector (for example plasmid or viral vector) and a DNA segment coding for a polypeptide, as described above. In a preferred embodiment, the DNA segment is present in the vector operably linked to a promoter.

In a further embodiment, the present invention relates to a host cell containing the above described recombinant DNA molecule or DNA segment. Suitable host cells include prokaryotes (such as bacteria, including *Escherichia coli*) and both lower eukaryotes (for example yeast) and higher eukaryotes (for example, algae, plant or animal cells). Introduction of the recombinant molecule into the cell can be effected using methods known in the art such as, but not limited to, transfection, transformation, micro-injection, gene bombardment etc. The cell thus made to contain the above described recombinant DNA molecules may be grown to form colonies or may be made to differentiate to form a differentiated organism. The recombinant DNA molecule may be transiently contained (e.g., by a process known in the art as transient transfection) in the cell, nevertheless, it is preferred that the recombinant DNA molecule is stably contained (e.g., by a process known in the art as stable transfection) in the cell. Yet in a preferred embodiment the cell is endogenously producing, or is made by genetic engineering means to produce, β-carotene, and the cell contains endogenous or genetically engineered β-carotene hydroxylase activity. Such a cell may be used as a food additive for animal (e.g., salmon) and human consumption. Furthermore, such a cell may be used for extracting astaxanthin and/or other xanthophylls, as described hereinbelow.

In a further embodiment, the present invention relates to a host transgenic organism (e.g., a higher plant or animal) containing the above described recombinant DNA molecule or the above described DNA segment in its cells. Introduction of the recombinant molecule or the DNA segment into the host transgenic organism can be effected using methods known in the art. Yet, in a preferred embodiment the host organism is endogenously producing, or is made by genetic engineering means to produce, β-carotene and, also preferably the host organism contains endogenous or genetically engineered β-carotene hydroxylase activity. Such an organism may be used as a food additive for animal (e.g., salmon) and human consumption. Furthermore, such an organism may be used for extracting astaxanthin and/or other xanthophylls, as described hereinbelow.

In another embodiment, the present invention relates to a method of producing astaxanthin using the above described host cell or transgenic organism. In yet another embodiment, the present invention relates to a method of producing xanthophylls such as canthaxanthin, echinenone, cryptoxanthin, isocryptoxanthin, hydroxyechinenone, zeaxanthin, adonirubin, 3-hydroxyechinenone, 3'-hydroxyechinenone and/or adonixanthin using the above described host cell or transgenic organism. For these purposes provided is a cell or a transgenic organism as described above. The host cell or organism are made to grow under conditions favorable of producing astaxanthin and the above listed additional xanthophylls which are than extracted by methods known in the art.

In yet another embodiment, the present invention relates to a transgenic plant expressing a transgene coding for a polypeptide including an amino acid sequence corresponding to *Haematococcus pluvialis* crtO gene, allelic and species variants or functional naturally occurring or man-induced variants thereof. Preferably the expression is highest in chromoplasts-containing tissues.

In yet another embodiment, the present invention relates to a recombinant DNA vector which includes a first DNA segment encoding a polypeptide for directing a protein into plant chloroplasts or chromoplasts (e.g., derived from the Pds gene of tomato) and an in frame second DNA segment encoding a polypeptide including an amino acid sequence corresponding to *Haematococcus pluvialis* crtO gene, allelic and species variants or functional naturally occurring and man-induced variants thereof.

In yet another embodiment, the present invention relates to a recombinant DNA vector which includes a first DNA segment including a promoter highly expressible in plant chloroplasts or chromoplasts-containing tissues (e.g., derived from the Pds gene of tomato) and a second DNA segment encoding a polypeptide including an amino acid sequence corresponding to *Haematococcus pluvialis* crtO gene, allelic and species variants or functional naturally occurring and man-induced variants thereof.

Reference in now made to the following examples, which together with the above descriptions, illustrate the invention.

EXAMPLES

The following protocols and experimental details are referenced in the Examples that follow:

Algae and growth conditions. *Haematococcus pluvialis* (strain 34/7 from the Culture Collection of Algae and Protozoa, Windermere, UK) was kindly provided by Dr. Andrew Young from the Liverpool John Moores University. Suspension cultures of the alga were grown in a liquid medium as described by Nichols and Bold [see, Nichols H W, Bold H C (1964) *Trichsarcina polymorpha* gen et sp nov J Phycol 1: 34–39]. For induction of astaxanthin biosynthesis cells were harvested, washed in water and resuspended in a nitrogen-depleted medium. The cultures were maintained in 250 ml Erlenmeyer flasks under continuous light (photon flux of 75 $\mu E/m^2/s$), at 25° C., on a rotary shaker at 80 rpm.

Construction of cDNA library. The construction of a cDNA library from *Haematococcus pluvialis* was described in detail by Lotan and Hirschberg (1995) FEBS letters 364: 125–128. Briefly, total RNA was extracted from algal cells grown for 5 days under nitrogen-depleted conditions (cell color brown-red). Cells from a 50 ml culture were harvested and their RNA content was extracted using Tri reagent (Molecular Research Center, INC.). Poly-An RNA was isolated by two cycles of fractionation on oligo dT-cellulose (Boehringer). The final yield was 1.5% of the total RNA. The cDNA library was constructed in a Uni-ZAP™ XR vector, using a ZAP-cDNA synthesis kit (both from Stratagene). *Escherichia coli* cells of strain XL1-Blue MRF' (Stratagene) were used for amplification of the cDNA library.

Figure 4:
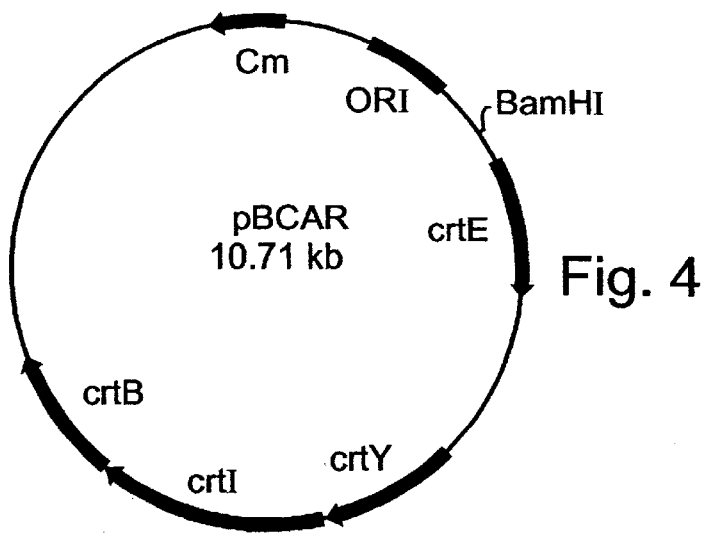
FIG. 4 is a schematic depiction of a pACYC184 derived plasmid designated pBCAR and includes the genes crtE, crtB, crtI and crtY of *Erwinia herbicola*, which genes are required for production of β-carotene in *Escherichia coli* cells.

Plasmids and *Escherichia coli* strains. Plasmid pPL376, which contains the genes necessary for carotenoid biosynthesis in the bacterium *Erwinia herbicola* was obtained from Tuveson [for further details regarding plasmid pPL376 see, Tuveson R W, Larson R A & Kagan J (1988) Role of cloned carotenoid genes expressed in *Escherichia coli* in protecting against inactivation by near-UV light and specific phototoxic molecules. J Bacteriol 170: 4675–4680]. Cells of *Escherichia coli* strain JM109 that carry the plasmid pPL376 accumulate the bright yellow carotenoid, zeaxanthin glycoside. In a first step, a 1.1 kb SalI—SalI fragment was deleted from this plasmid to inactivate the gene crtX, coding for zeaxanthin glucosyl transferase. In a second step, partial BamHI cleavage of the plasmid DNA, followed by self ligation, deleted a 0.8 kb fragment which inactivated crtZ, encoding β-carotene hydroxylase. A partial BglII cleavage generated a fragment of 7.4 kb which was cloned in the BamHI site of the plasmid vector pACYC184. As shown in FIG. 4, the resulting recombinant plasmid, which carried the genes crtE, crtB, crtI and crtY, was designated pBCAR [Lotan and Hirschberg (1995) FEBS letters 364: 125–128].

Plasmid pBCAR was transfected into SOLR strain cells of *Escherichia coli* (Stratagene). Colonies that appeared on chloramphenicol-containing Luria Broth (LB) medium [described in Sambrook et al., Molecular Cloning; A Laboratory Manual. Cold Spring Harbor Laboratory, Cold Spring Harbor, N.Y. 1989], carried this plasmid and developed a deep yellow-orange color due to the accumulation of β-carotene.

Figure 5:
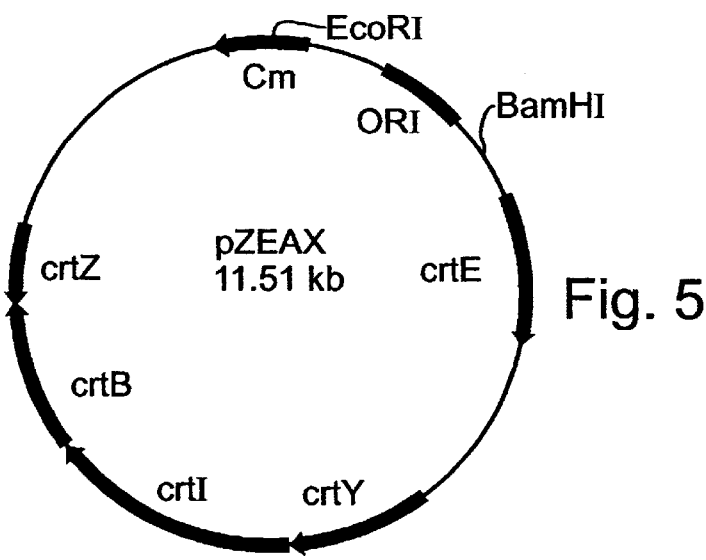
FIG. 5 is a schematic depiction of a pACYC184 derived plasmid designated pZEAX and includes the genes crtE, crtB, crtI, crtY and crtZ from *Erwinia herbicola*, which genes are required for production of zeaxanthin in *Escherichia coli* cells.

As shown in FIG. 5, an additional plasmid, designated pZEAX, which allows for zeaxanthin synthesis and accumulation in *Escherichia coli* was constructed [this plasmid is described in details in Lotan and Hirschberg (1995) FEBS letters 364: 125–128]. SOLR strain *Escherichia coli* cells were used as a host for the pZEAX plasmid. *Escherichia coli* cells were grown on LB medium (see above), at 37° C. in the dark on a rotary shaker at 225 rpm. Ampicillin (50 μg/ml) and/or chloramphenicol (30 μg/ml) (both from Sigma) were added to the medium for selection of appropriate transformed cells.

Figure 6:
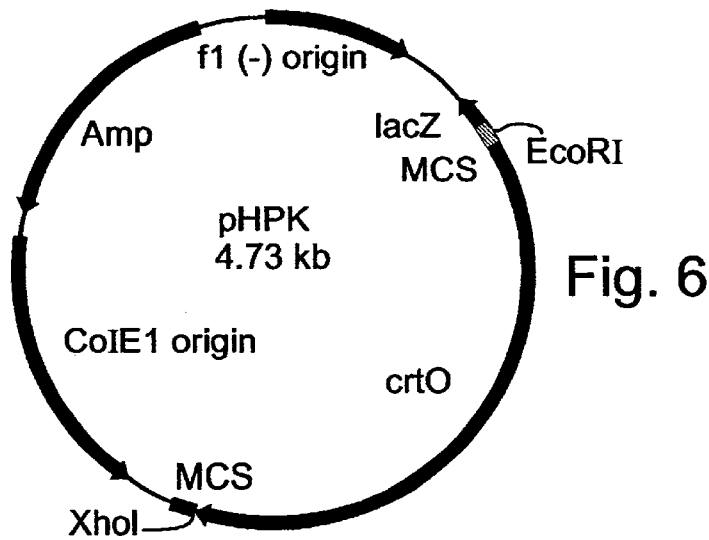
FIG. 6 is a schematic depiction of a pBluescriptSK⁻ derived plasmid designated pHPK, containing a full length cDNA insert encoding a β-carotene C-4-oxygenase enzyme from *Haematococcus pluvialis*, designated crtO and set forth in SEQ ID NO:1, which cDNA was identified by color complementation of *Escherichia coli* cells.
Figure 7:
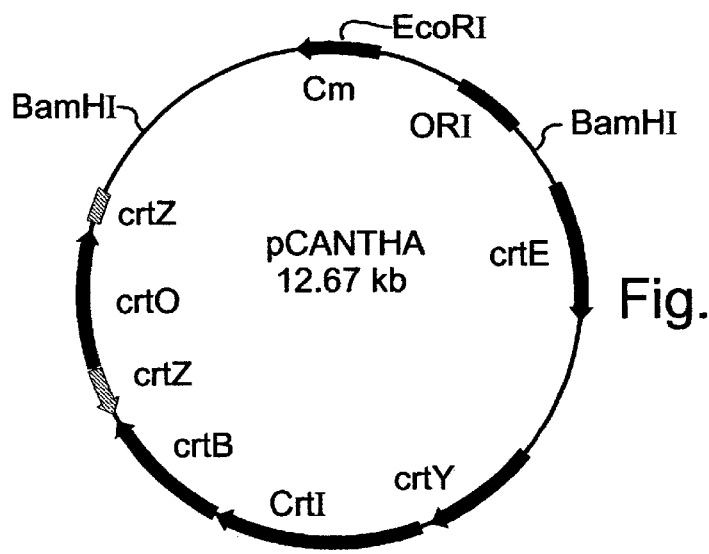
FIG. 7 is a schematic depiction of a $pACYC_{184}$ derived plasmid designated pCANTHA which was derived by inserting a 1.2 kb PstI—PstI DNA fragment, containing the cDNA encoding the β-C-4-oxygenase from *Haematococcus pluvialis* isolated from the plasmid pHPK of FIG. 6 and inserted into a PstI site in the coding sequence of the crtZ gene in the plasmid pZEAX of FIG. 5; this recombinant plasmid carries the genes crtE, crtB, crtI, crtY of *Erwinia herbicola* and the crtO gene of *Haematococcus pluvialis*, all required for production of canthaxanthin in *Escherichia coli* cells.

As shown in FIG. 6, a plasmid, pHPK, containing the full length cDNA of the β-carotene C-4-oxygenase enzyme was identified by color complementation as described by Lotan and Hirschberg (1995) FEBS letters 364: 125–128 (see description herein below). A 1.2 kb PstI—PstI DNA fragment, containing the cDNA of the β-C-4-oxygenase from *Haematococcus pluvialis*, was isolated from plasmid pHPK and inserted into a PstI site in the coding sequence of the crtZ gene in the plasmid pZEAX. This recombinant plasmid was designated pCANTHA and is shown in FIG. 7.

Figure 8:
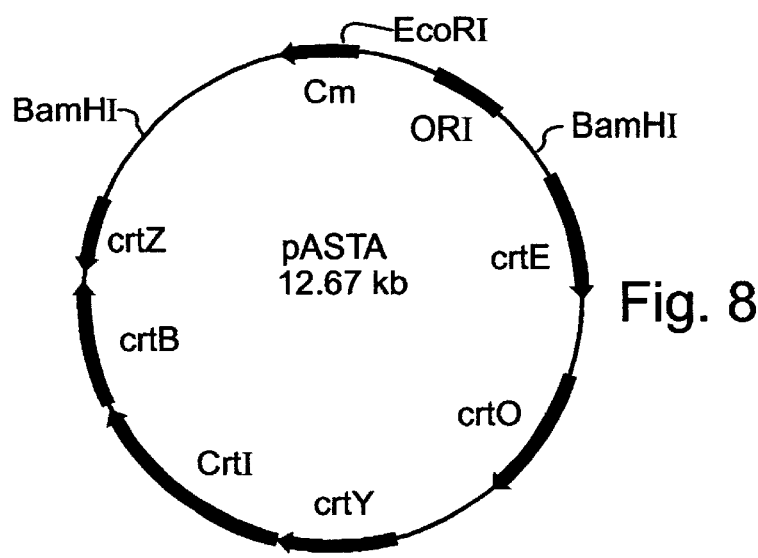
FIG. 8 is a schematic depiction of a pACYC 184 derived plasmid designated pASTA which was derived by inserting the 1.2 kb PstI—PstI DNA fragment, containing the cDNA of the β-C-4-oxygenase from *Haematococcus pluvialis* isolated from the plasmid pHPK of FIG. 6 and inserted into a PstI site which exists 600 bp downstream of the crtE gene in the plasmid pZEAX of FIG. 5; this recombinant plasmid carries the genes crtE, crtB, crtI, crtY, crtZ of *Erwinia herbicola* and the crtO gene of *Haematococcus pluvialis*, all required for production of astaxanthin in *Escherichia coli* cells.

The same 1.2 kb PstI—PstI fragment was also inserted into a PstI site which exists 600 bp downstream of the crtE gene in the plasmid pZEAX. The resulting recombinant plasmid was designated pASTA and is shown in FIG. 8.

Figure 9:
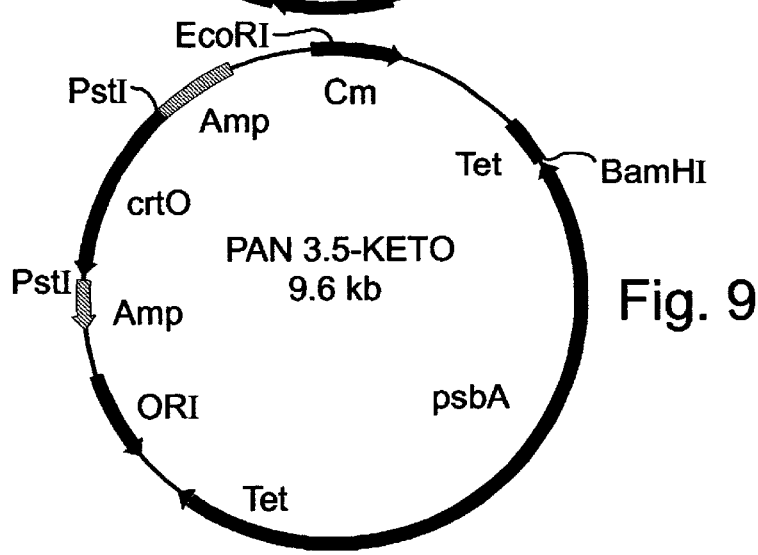
FIG. 9 is a schematic depiction of a pBR328 derived plasmid designated PAN3.5-KETO which was derived by inserting the 1.2 kb PstI—PstI DNA fragment, containing the cDNA of the β-C-4-oxygenase from *Haematococcus pluvialis* isolated from the plasmid pHPK of FIG. 6 and inserted into a PstI site which exists in a β-lactamase gene in a plasmid designated pPAN35D5 [described in Hirschberg J, Ohad N, Pecker I and Rahat A (1987) Isolation and characterization of herbicide resistant mutants in the cyanobacterium Synechococcus R2. Z. Naturforsch 42c: 102–112], which carries the psbAI gene from the cyanobacterium Synechococcus PCC7942 in the plasmid vector pBR328 [see, Hirschberg J, Ohad N, Pecker I and Rahat A (1987) Isolation and characterization of herbicide resistant mutants in the cyanobacterium Synechococcus R2. Z. Naturforsch 42c: 102–112]; this recombinant plasmid carries the crtO gene of *Haematococcus pluvialis*, required for production of astaxanthin in Synechococcus PCC7942 cells.

The same 1.2 kb PstI—PstI fragment was also inserted into a PstI site which exists in the β-lactamase gene in the plasmid pPAN35D5 [Hirschberg J, Ohad N, Pecker I and Rahat A (1987) Isolation and characterization of herbicide resistant mutants in the cyanobacterium Synechococcus R2. Z. Naturforsch 42c: 102–112], which carries the psbAI gene from the cyanobacterium Synechococcus PCC7942 in the plasmid vector pBR328 [Hirschberg J, Ohad N, Pecker I and Rahat A (1987) Isolation and characterization of herbicide resistant mutants in the cyanobacterium Synechococcus R2. Z. Naturforsch 42c: 102–112]. This plasmid was designated PAN3.5-KETO and is shown in FIG. 9. This plasmid was used in the transformation of Synechococcus PCC7942 cells following procedures described by Golden [Golden SS (1988) Mutagenesis of cyanobacteria by classical and gene-transfer-based methods. Methods Enzymol 167: 714–727].

Excision of phage library and screening for a β-carotene oxygenase gene. Mass excision of the cDNA library, which was prepared as described hereinabove, was carried out using the ExAssist helper phage (Stratagene) in cells of SOLR strain of *Escherichia coli* that carried the plasmid pBCAR. The excised library in phagemids form was transfected into *Escherichia coli* cells strain XL1-Blue and the cells were plated on LB plates containing 1 mM isopropylthio-β-D-galactosidase (IPTG), 50 μg/ml ampicillin and 30 μg/ml chloramphenicol, in a density that yielded approximately 100–150 colonies per plate. The plates were incubated at 37° C. overnight and further incubated for two more days at room temperature. The plates were then kept at 4° C. until screened for changes in colony colors.

Figure 10:
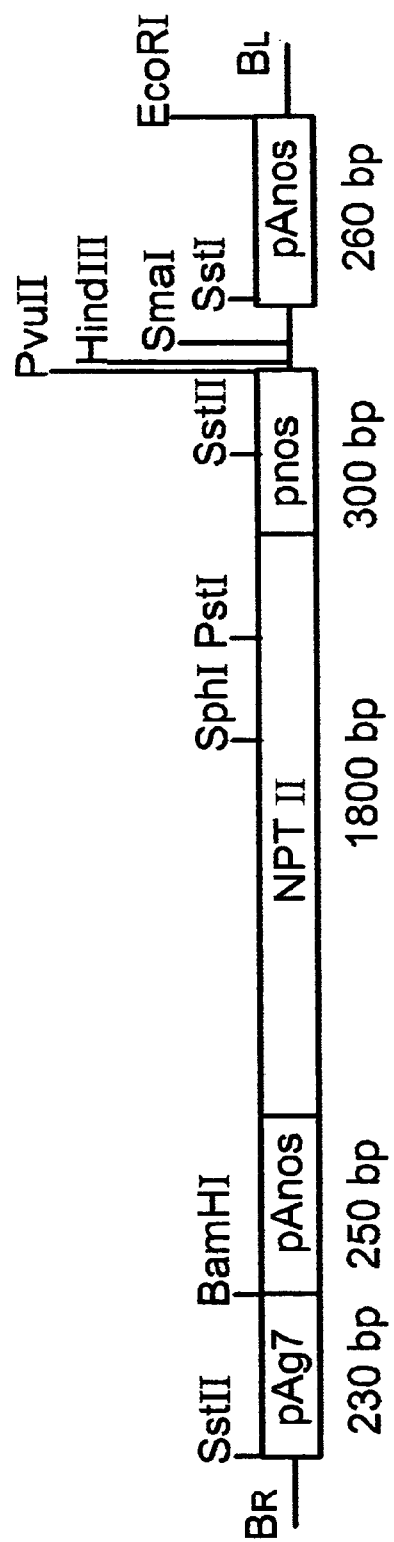
FIG. 10 is a schematic depiction of the T-DNA region of a Ti binary plasmid (*E. coli*, Agrobacterium) designated pBIB [described by Becker D (1990) Binary vectors which allow the exchange of plant selectable markers and reporter genes. Nucleic Acids Research 18:230] which is a derivative of the Ti plasmid pBI101 [described by Jeffesrson A R, Kavanagh T A and Bevan W M (1987) GUS fusions: β-glucuronidase as a sensitive and versatile gene fusion marker in higher plants. The EMBO J. 6: 3901–3907], wherein $B_R$ and $B_L$ are the right and left borders, respectively, of the T-DNA region, pAg7 is the polyadenylation site of gene 7 of Agrobacterium Ti-plasmid, pAnos is a 250 bp long DNA fragment containing the poly adenylation site of the nopaline synthase gene of Agrobacterium, NPT II is a 1,800 bp long DNA fragment coding for kanamycin resistance, pnos is a 300 bp long DNA fragment containing the promoter sequence of the nopaline synthase gene of Agrobacterium, whereas pAnos is a 300 bp long DNA fragment containing the poly adenylation site of the nopaline synthase gene of Agrobacterium.
Figure 11:
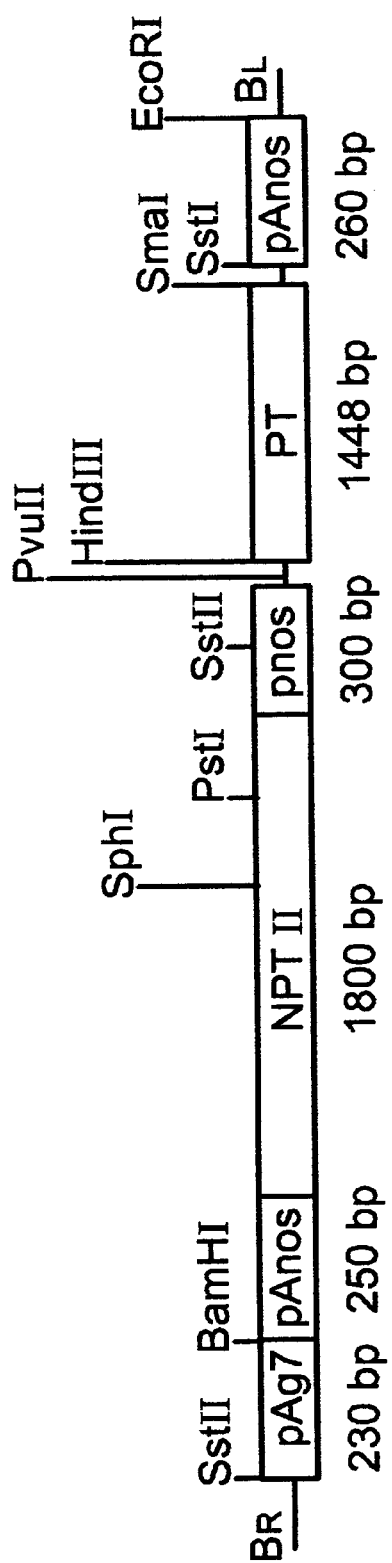
FIG. 11 is a schematic depiction of the T-DNA region of a Ti binary plasmid (*E. coli*, Agrobacterium) designated pPTBIB which was prepared by cloning a genomic DNA sequence of a tomato species *Lycopersicon esculentum* marked PT (nucleotides 1 to 1448 of the Pds gene as published in Mann V, Pecker I and Hirschberg J (1994) cloning and characterization of the gene for phytoene desaturase (Pds) from tomato (*Lycopersicon esculentum*). Plant Molecular Biology 24: 429–434), which contains the promoter of the Pds gene and the coding sequence for the amino terminus region of the polypeptide PDS that serve as a transit peptide for import into chloroplasts and chromoplasts, into a HindIII-SmaI site of the binary plasmid vector pBIB of FIG. 10, wherein $B_R$ and $B_L$, pAg7, pAnos, NPT II, pnos and pAnos are as defined above.

A plasmid for high expression of crtO in chromoplasts. As shown in FIGS. 10–11, a genomic DNA sequence of a tomato species *Lycopersicon esculentum* (nucleotides 1 to 1448 of the Pds gene [as published in Mann V, Pecker I and Hirschberg J (1994) cloning and characterization of the gene for phytoene desaturase (Pds) from tomato (*Lycopersicon esculentum*). Plant Molecular Biology 24: 429–434], which contains the promoter of the Pds gene and the coding sequence for the amino terminus region of the polypeptide PDS that serve as a transit peptide for import into chloroplasts and chromoplasts, was cloned into a HindIII-SmaI site of the binary plasmid vector pBIB, [described by Becker D (1990) Binary vectors which allow the exchange of plant selectable markers and reporter genes. Nucleic Acids Research 18:230], shown in FIG. 10. The recombinant plasmid was designated pPTBIB and is shown in FIG. 11.

Figure 12:
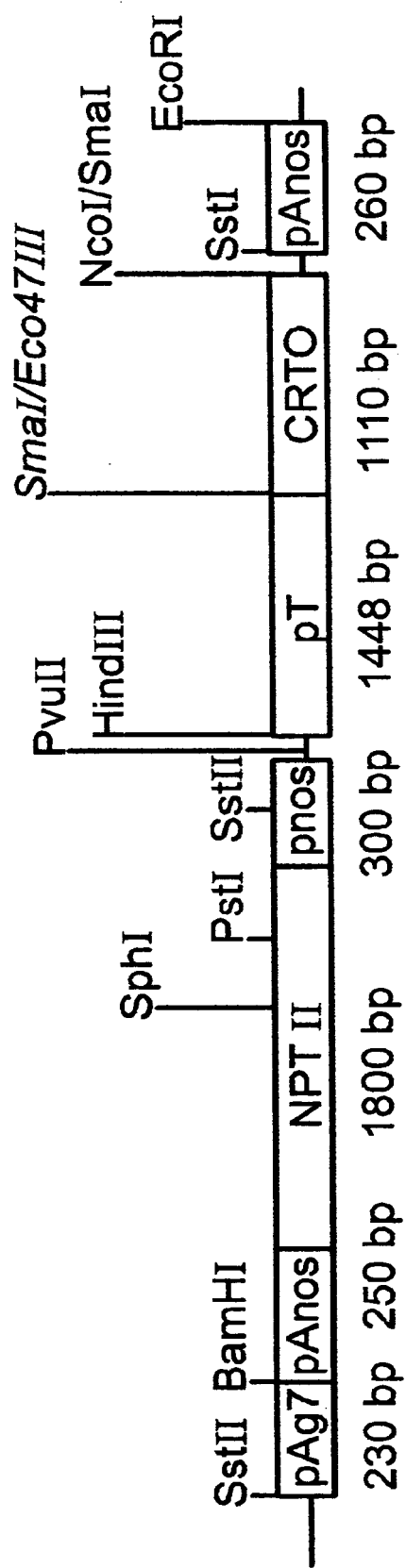
FIG. 12 is a schematic depiction of the T-DNA region of a Ti binary plasmid (*E. coli*, Agrobacterium) designated pPTCRTOBIB which was prepared by cloning a 1,110 nucleotide long Eco47III-NcoI fragment of the cDNA of crtO from *H. pluvialis* (nucleotides 211 to 1321 of SEQ ID NO:1) into the SmaI site of the plasmid pPTBIB of FIG. 11, such that the coding nucleotide sequence of the amino terminus of PDS is in the same reading frame of crtO, wherein $B_R$ and $B_L$, pAg7, pAnos, NPT II, pnos, and pAnos are as defined above, PT is the promoter and transit peptide coding sequences of Pds from tomato and CRTO is the nucleotide sequence of crtO from *H. pluvialis* (nucleotides 211 to 1321 of SEQ ID NO:1)

As shown in FIG. 12, a 1,110 nucleotide long Eco47III-NcoI fragment, containing the cDNA of crtO from *H. pluvialis* (nucleotides 211 to 1321 of SEQ ID NO:1) was subcloned into the SmaI site of the plasmid pPTBIB (FIG. 11) so that the coding nucleotide sequence of the amino terminus of Pds is in the same reading frame as crtO. The recombinant plasmid was designate pPTCRTOBIB.

Formation of transgenic higher plant. The DNA of pPTCRTOBIB was extracted from *E. coli* cells and was transferred into cells of *Agrobacterium tumefaciens* strain EHA105 [described by Hood E E, Gelvin S B, Melchers L S and Hoekema A (1993) Transgenic Research 2:208–218] using electroporation as described for *E. coli* [Dower J W, Miller F J and Ragdsale W C (1988) High efficiency transformation of *E. coli* by high voltage electroporation. Nuc. Acids Res. 18: 6127–6145]. Agrobacterium cells were grown at 28° C. in LB medium supplemented with 50 μg/ml streptomycin and 50 μg/ml kanamycin as selective agents. Cells of Agrobacterium carrying pPTCRTOBIB were harvested from a suspension culture at the stationary phase of growth and used for transformation as described by Horsch R B, Fry J E, Hoffmann N L, Eicholtz D, Rogers S G and Fraley R T, A simple and general method for transferring genes into plants. Science (1985) 227:1229–1231; and Jeffesrson A R, Kavanagh T A and Bevan W M (1987) GUS fusions: β-glucuronidase as a sensitive and versatile gene fusion marker in higher plants. The EMBO J. 6: 3901–3907.

Leaf explants of *Nicotiana tobaccum* strain NN were infected with the transformed Agrobacterium cells and kanamycin-resistant transgenic plants were regenerated according to protocols described by Horsch et al. (1985) and Jefferson et al. (1987) cited above.

Figure 13:
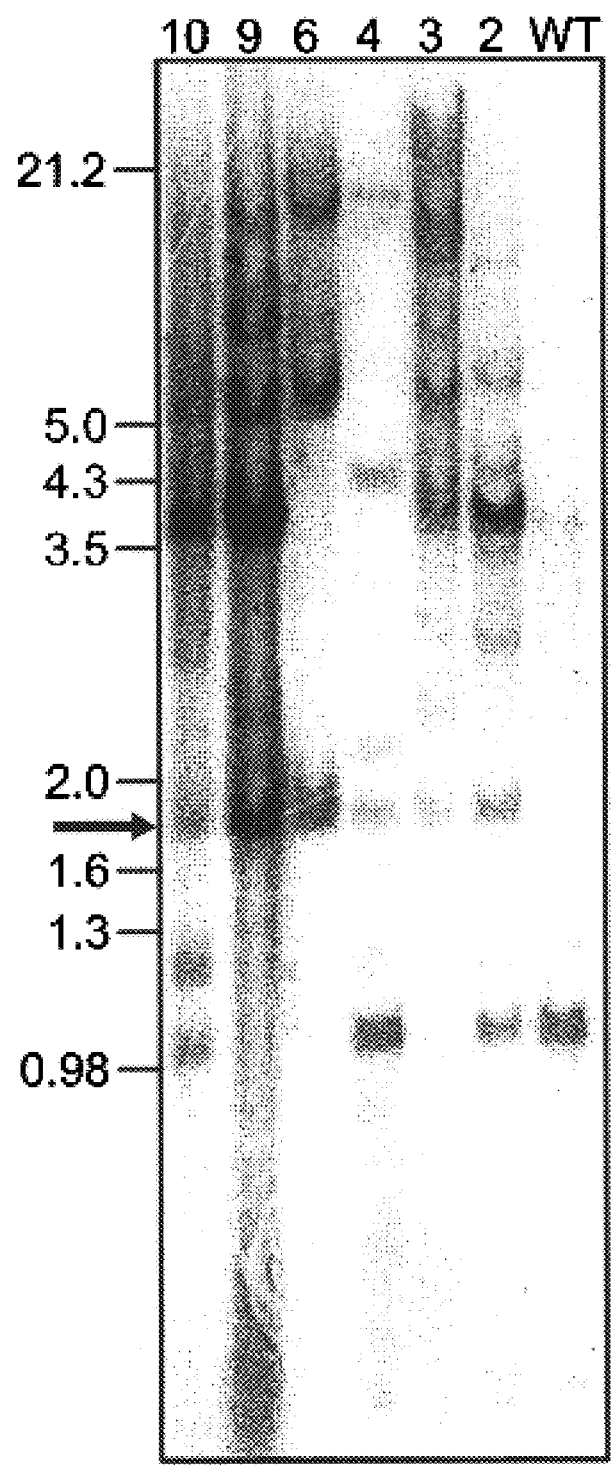
FIG. 13 shows a Southern DNA blot analysis of HindIII-digested genomic DNA extracted from wild type (WT) and crtO tobacco transgenic plants, designated 2, 3, 4, 6, 9 and 10, according to the present invention, using the crtO cDNA as a radioactive probe essentially as described in Sambrook et al., Molecular Cloning; A Laboratory Manual. Cold Spring Harbor Laboratory, Cold Spring Harbor, N.Y. 1989, wherein the size of marker (M) DNA fragments in kilobase pairs (kb) is indicated on the left as well as the expected position (arrow) of an internal T-DNA HindIII fragment as was deduced from the sequence of pPTPDSBIB shown in FIG. 12 which contain the crtO cDNA sequence.

With reference now to FIG. 13, the presence of the DNA sequence of the crtO gene-construct in the fully developed regenerated plants was determined by DNA Southern blot analysis. To this end DNA was extracted from the leaves [according to a protocol described by Kanazawa and Tsutsumi (1992) Extraction of restrictable DNA from plants of the genus Nelumbo. Plant Molecular Biology Reports 10: 316–318], digested with the endonuclease HindIII, the fragments were size separated by gel electrophoresis and hybridized with radioactively labeled crtO sequence (SEQ ID NO: 1).

It was determined that each transgenic plant that was examined contained at least one copy of the crtO DNA sequence, yielding a 1.75 kb band (arrow), originating from an internal HindIII—HindIII fragment of the T-DNA of pPTCRTOBIB, additional bands originating from partial digestion, additional band/s whose sizes vary, depending on the position of insertion in the plant genome and a 1.0 kb band originating from the tobacco plant itself which therefore also appears in the negative control WT lane.

Sequence analysis. DNA sequence analysis was carried out by the dideoxy method [see, Sanger F, Nicklen S & Coulsen A R (1977) DNA sequencing with chain termination inhibitors. Proc Natl Acad Sci USA 74: 5463–5467].

Carotenoids analysis. Aliquots of *Escherichia coli* cells which were grown in liquid in LB medium were centrifuged at 13,000 g for 10 minutes, washed once in water and re-centrifuged. After removing the water the cells were resuspended in 70 μl of acetone and incubated at 65° C. for 15 minutes. The samples were centrifuged again at 13,000 g for 10 minutes and the carotenoid-containing supernatant was placed in a clean tube. The carotenoid extract was blown to dryness under a stream of nitrogen ($N_2$) gas and stored at −20° C. until required for analysis. Carotenoids from plant tissues were extracted by mixing 0.5–1.0 gr of tissue with 100 μl of acetone followed by incubation at 65° C. for 15 minutes and then treating the samples as described above.

High-performance liquid chromatography (HPLC) of the carotenoid extracts was carried out using an acidified reverse-phase C18 column, Spherisorb ODS-2 (silica 5 μm 4.6 mm×250 mm) (Phenomenex®). The mobile phase was pumped by triphasic Merck-Hitachi L-6200A high pressure pumps at a flow rate of 1.5 ml/min. The mobile phase consisted of an isocratic solvent system comprised of hexane/dichloromethane/isopropyl alcohol/triethylamine (88.5:10:1.5:0.1, v/v). Peaks were detected at 470 nm using a Waters 996 photodiode-array detector. Individual carotenoids were identified by their retention times and their typical absorption spectra, as compared to standard samples of chemically pure β-carotene, zeaxanthin, echinenone, canthaxanthin, adonirubin and astaxanthin (The latter four were kindly provided by Dr. Andrew Young from Liverpool John Moores University).

Thin layer chromatography (TLC) was carried out using silica gel 60 F254 plates (Merck), using ethyl acetate/benzene (7:3, v/v) as an eluent. Visible absorption spectra were recorded with a Shimadzu UV-160A spectrophotometer. All spectra were recorded in acetone. Spectral fine structure was expressed in terms of %III/II [Britton, G. (1995). UV/Visible Spectroscopy. In: Carotenoids; Vol IB, Spectroscopy. Eds. Britton G, Liaaen-Jensen S and Pfander H. Birkhauser Verlag, Basel. pp. 13–62].

Figure 14:
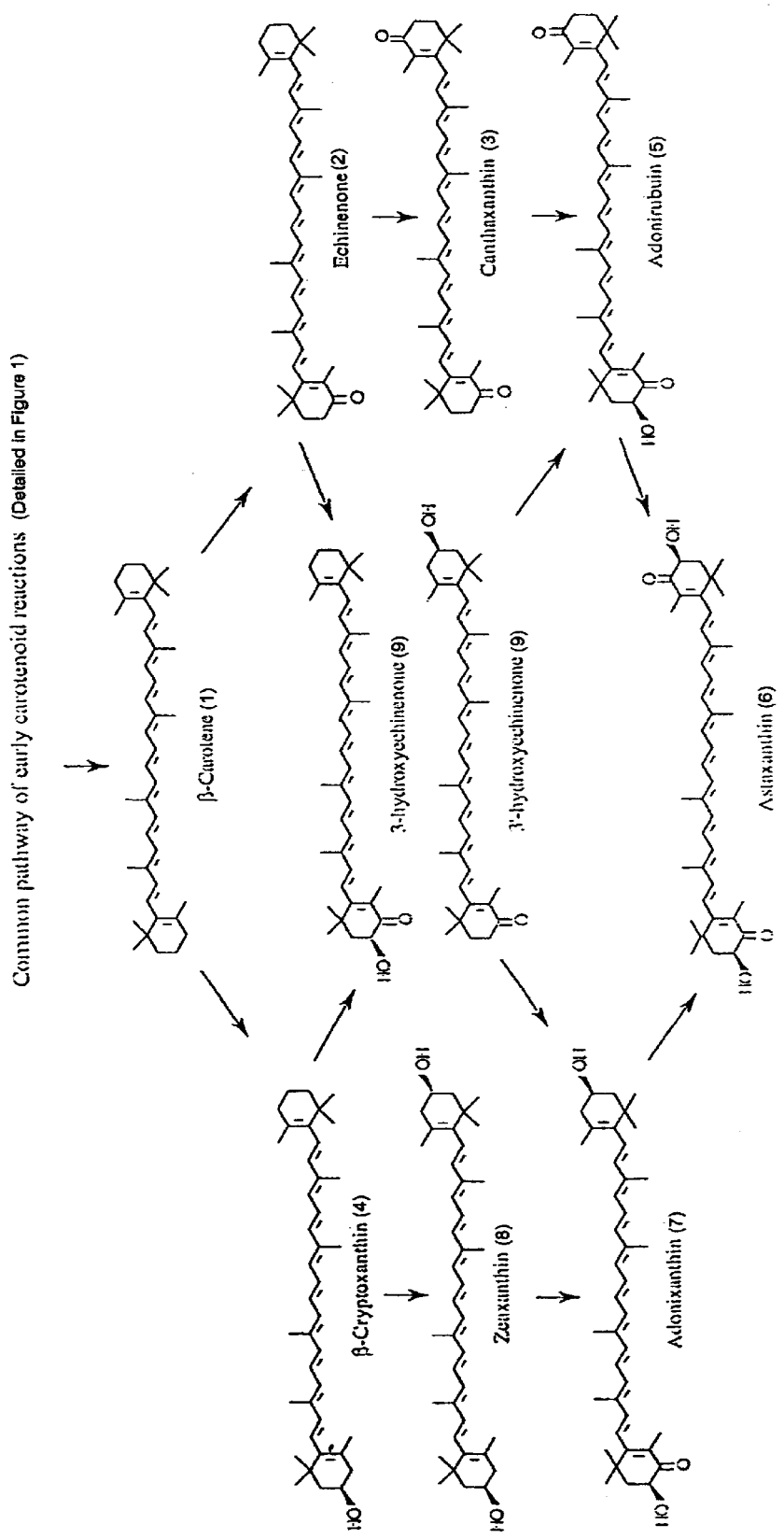
FIG. 14 shows a biosynthesis pathway of astaxanthin.

Isolation and identification of the carotenoids extracted from cells of *E. coli* are treated in order of increasing adsorption (decreasing $R_f$ values) on silica TLC plates. Carotenoids structure and the biosynthesis pathway of astaxanthin are given in FIG. 14. The following details refer to the carotenoids numbered 1 through 9 in FIG. 14.

β-Carotene (1). $R_f$0.92 inseparable from authentic (1). $R_t$. VIS $\lambda_{max}$ nm: (428), 452, 457, %III/II=0.

Echinenone (2). $R_f$0.90 inseparable from authentic (2). $R_t$. VIS $\lambda_{max}$ nm: 455, %III/II=0.

Canthaxanthin (3). $R_f$0.87. inseparable from authentic (3). $R_t$. VIS $\lambda_{max}$ nm: 470, %III/II=0.

β-Cryptoxanthin (4). $R_f$0.83. $R_t$. VIS $\lambda_{max}$ nm: (428), 451, 479, %III/II=0.

Adonirubin (5). $R_f$0.82 inseparable from authentic (5). $R_t$. VIS $\lambda_{max}$ nm: 476, %III/II=0.

Astaxanthin (6). $R_f$0.79 inseparable from authentic (6). $R_t$. VIS $\lambda_{max}$ nm: 477, %III/II=0.

Adonixanthin (7). $R_f$0.72. $R_t$. VIS $\lambda_{max}$ nm: 464, %III/II=0.

Zeaxanthin (8). $R_f$0.65 inseparable from authentic (8). $R_t$. VIS $\lambda_{max}$ nm: (428), 451, 483, %III/II=27.

Hydroxyechinenone (9). Rf0.80, Rt, 3.0. VIS $\lambda_{max}$ nm: 464, %III/II=0.

Chirality configuration. Chirality configuration of astaxanthin was determined by HPLC of the derived diastereoisomeric camphanates of the astaxanthin [Renstrom B, Borch G, Skulberg M and Liaaen-Jensen S (1981) Optical purity of (3S,3S')-astaxanthin from *Haematococcus pluvialis*. Phytochem 20: 2561–2565]. The analysis proved that the *Escherichia coli* cells synthesize pure (3S,3'S) astaxanthin.

EXAMPLE 1

Cloning the β-C-4-oxygenase Gene

A cDNA library was constructed in Lambda ZAP II vector from poly-An RNA of *Haematococcus pluvialis* cells that had been induced to synthesize astaxanthin by nitrogen deprivation as described hereinabove. The entire library was excised into β-carotene-accumulating cells of *Escherichia coli*, strain SOLR, which carried plasmid pBCAR (shown in FIG. 4). Screening for a β-carotene oxygenase gene was based on color visualization of colonies of size of 3 mm in diameter. Astaxanthin and other oxygenated forms of β-carotene (i.e., xanthophylls) have distinct darker colors and thus can be detected from the yellow β-carotene background. The screening included approximately 100,000 colonies which were grown on LB medium plates containing ampicillin and chloramphenicol that selected for both the Lambda ZAP II vector in its plasmid propagating form and the pBCAR plasmid. Several colonies showed different color tones but only one exhibited a conspicuous brown-red pigment. This colony presumed to contain a xanthophyll biosynthesis gene was selected for further analysis described hereinbelow in the following Examples.

EXAMPLE 2

Analysis of the β-C-4-oxygenase Activity in *Escherichia coli*

The red-brown colony presumed to contain a xanthophyll biosynthesis gene (see Example 1 above) was streaked and further analyzed. First, the recombinant ZAP II plasmid carrying the cDNA clone that was responsible for xanthophyll synthesis in *Escherichia coli* was isolated by preparing plasmid DNA from the red-brown colony, transfecting it to *Escherichia coli* cells of the strain XL1-Blue and selection on ampicillin-containing medium. This plasmid, designated pHPK (pHPK is a Lambda ZAP II vector containing an insert isolated from the red-brown colony), was used to transform β-carotene-producing *Escherichia coli* cells (*Escherichia coli* SOLR strain that carry the plasmid pBCAR shown in FIG. 4) resulting in the formation of red-brown colonies. Carotenoids from this transformant, as well as from the host cells (as control) were extracted by acetone and analyzed by HPLC.

HPLC analysis of carotenoids of the host bacteria which synthesized β-carotene (*Escherichia coli* SOLR strain that carry the plasmid pBCAR shown in FIG. 4), as compared with a brown-red colony, revealed that only traces of β-carotene were observed in the transformant cells while a new major peak of canthaxanthin and another minor peak of echinenone appeared [described in detail by Lotan and Hirschberg (1995) FEBS letters 364: 125–128]. These results indicate that the cDNA in plasmid pHPK, designated crtO encodes an enzyme with β-C-4-oxygenase activity, which converts β-carotene to canthaxanthin via echinenone (see FIG. 14). It is, therefore concluded that a single enzyme catalyzes this two-step ketonization conversion by acting symmetrically on the 4 and 4' carbons of the β- and β'-rings of β-carotene, respectively.

EXAMPLE 3

Production of Astaxanthin in *Escherichia coli* Cells

To determine whether β-carotene hydroxylase (e.g., a product of the crtZ gene of *Erwinia herbicola*) can convert thus produced canthaxanthin to astaxanthin and/or whether zeaxanthin converted from β-carotene by β-carotene hydroxylase can be converted by β-C-4-oxygenase to astaxanthin, the crtO cDNA of *Haematococcus pluvialis* thus isolated, was expressed in *Escherichia coli* cells together with the crtZ gene of *Erwinia herbicola*. For this purpose, *Escherichia coli* cells of strain SOLR were transfected with either plasmid pASTA alone containing, as shown in FIG. 8, both crtZ and crtO or, alternatively with both plasmids, pHPK containing, as shown in FIG. 6, crtO, and pZEAX containing, as shown in FIG. 5, crtZ. Carotenoids in the resulting transformed cells were extracted and analyzed by HPLC as described above. The results, given in Table 1, show the composition of carotenoids extracted from the cells containing the plasmid pASTA. Similar carotenoid composition is found in *Escherichia coli* cells which carry both pHPK and pZEAX.

TABLE 1

| Carotenoid | % of total carotenoid composition |
| --- | --- |
| β-Carotene | 8.0 |
| Echineone | 1.7 |
| β-Cryptoxanthin | 4.2 |
| Canthaxanthin | 4.2 |
| Zeaxanthin | 57.8 |
| Adonirubin | 1.0 |
| Adonixanthin | 17.9 |
| Astaxanthin | 5.2 |

The results presented in Table 1, prove that carotenoids possessing either a β-end group or a 4-keto-β-end group act as substrates for the hydroxylation reactions catalyzed by crtZ gene product at carbons C-3 and C-3'. The hydroxylation of β-carotene and canthaxanthin results in the production of zeaxanthin and astaxanthin, respectively. These hydroxylations result in the production of astaxanthin and the intermediate ketocarotenoids, 3-hydroxyechinenone, adonixanthin and adonirubin. These results further demonstrate that astaxanthin can be produced in heterologous cells by expressing the gene crtO together with a gene that codes for a β-carotene hydroxylase.

EXAMPLE 4

Sequence Analysis of the Gene for β-Carotene C-4-Oxygenase

The full length, as was determined by the presence of a poly A tail, of the cDNA insert in plasmid pHPK (1771 base pairs) was subjected to nucleotide sequence analysis. This sequence, set forth in SEQ ID NO:1, and its translation to an amino acid sequence set forth in SEQ ID NO:3 (329 amino acids), were deposited in EMBL database on May 1, 1995, and obtained the EMBL accession numbers X86782 and X86783, respectively.

An open reading frame (ORF) of 825 nucleotides (nucleotides 166 through 1152 in SEQ ID NO:3) was identified in this sequence. This ORF codes for the enzyme β-carotene C-4-oxygenase having 329 amino acids set forth in SEQ ID NO:4, as proven by its functional expression in *Escherichia coli* cells (see Example 3 above). The gene for this enzyme was designated crtO.

EXAMPLE 5

Transformation of Cyanobacteria with crtO

The plasmid DNA of pPAN3.5-KETO, shown in FIG. 9, was transfected into cells of the cyanobacterium Synechococcus PCC7942 according to the method described by Golden [Golden S S (1988) Mutagenesis of cyanobacteria by classical and gene-transfer-based methods. Methods Enzymol 167: 714–727]. The cyanobacterial cells were plated on BG11 medium-containing petri dishes that contained also chloramphenicol. Colonies of chloramphenicol-resistant Synechococcus PCC7942 which appeared after ten days were analyzed for their carotenoid content. As detailed in Table 2 below, HPLC analysis of these cells revealed that the major carotenoid components of the cells was β-carotene, echinenone, canthaxanthin, adonirubin and astaxanthin. A similar analysis of the wild type strain and of Synechococcus PCC7942 transfected with a plasmid in which the orientation of the crtO gene is reversed (not shown), which is therefore not capable of producing an active protein, did not revealed production of echinenone, canthaxanthin, adonirubin and astaxanthin.

These result prove that crtO of *Haematococcus pluvialis* can be expressed in cyanobacteria and that its expression provided a β-C-4-oxygenase enzymatic activity needed for the conversion of β-carotene to canthaxanthin. This result further demonstrates that the endogenous β-carotene hydroxylase of Synechococcus PCC7942 is able to convert thus produced canthaxanthin to astaxanthin. Since the carotenoid biosynthesis pathway is similar in all green photosynthetic organism [see FIGS. 1 and 10 and, Pecker I, Chamovitz D, Linden H, Sandmann G and Hirschberg J (1992) A single polypeptide catalyzing the conversion of phytoene to ζ-carotene is transcriptionally regulated during tomato fruit ripening. Proc Natl Acad Sci USA 89: 4962–4966] it is deduced that astaxanthin can be produced in algae, and higher plants by expressing crtO in any tissue that express also the endogenous β-carotene hydroxylase. It is further deduced that astaxanthin can be produced by any organism provided it contains either endogenous or engineered β-carotene biosynthesis pathway, by expressing crtO in any tissue that express either endogenous or genetically engineered β-carotene hydroxylase.

TABLE 2

| Carotenoid | % of total carotenoid composition |
| --- | --- |
| β-Carotene | 31.5 |
| Echinenone | 18.5 |
| Canthaxanthin | 16.1 |
| Zeaxanthin | 22.3 |
| Adonirubin | 6.0 |
| Astaxanthin | 5.6 |

EXAMPLE 6

Determining the Chirality Configuration of Astaxanthin Produced in Heterologous Systems The chirality configurations of astaxanthin produced by *Escherichia coli* cells, as described under Example 3 hereinabove, and by cyanobacterium Synechococcus PCC7942 cells, as described in Example 5 hereinabove, were determined by HPLC of the derived diastereoisomeric camphanates of the astaxanthin [Renstrom B, Borch G, Skulberg M and Liaaen-Jensen S (1981) Optical purity of (3S,3S')-astaxanthin from *Haematococcus pluvialis*. Phytochem 20: 2561–2565]. The analysis proved that the *Escherichia coli* and Synechococcus PCC7942 cells described above, synthesize pure (3S,3'S) astaxanthin.

EXAMPLE 7

Transformation of a Higher Plant with crtO

Producing natural astaxanthin in higher plants has two anticipated benefits. First, as a pure chemical, astaxanthin is widely used as feed additive for fish. It is a potential food colorant suitable for humans consumption and has potential applications in the cosmetic industry. Second, inducing astaxanthin biosynthesis in vivo in flowers and fruits will provide attractive pink/red colors which will increase their appearance and/or nutritious worth.

In flowers and fruits carotenoids are normally synthesized and accumulated to high concentration in chromoplasts, a typical pigment-containing plastids, thus providing typical intense colors to these organs. Inducing synthesis of astaxanthin in chromoplasts enables the accumulation of high concentration of this ketocarotenoid. Over-expression of carotenoid biosynthesis genes which results in elevated concentrations of carotenoids in chloroplasts, or other alterations in carotenoid composition in chloroplasts may damage the thylakoid membranes, impair photosynthesis and thus is deleterious to the plants. In contrast, increase of carotenoid concentration or alteration in carotenoid composition in chromoplasts do not affect the viability of the plant nor the yield of fruits and flowers.

Thus, gene-transfer technology was used to implant the crtO gene isolated from the alga *Haematococcus pluvialis*, as described, into a higher plant, in such a way that its expression is up-regulated especially in chromoplast-containing cells.

To this end, a T-DNA containing binary plasmid vector as shown in FIG. 12 was assembled in *E. coli* from the promoter and coding DNA sequences of the transit peptide encoded by the Pds gene from a tomato species *Lycopersicon esculentum*, linked to the coding DNA sequence of crtO from *H. pluvialis*. Upon stable transfer of this DNA construct via Agrobacterium-mediated transformation into a tobacco (*Nicotiana tabacum* NN) plant to form a transgenic plant, as described under methods above, the plant acquired the ability to produce ketocarotenoids especially in flower tissues (chromoplast-containing cells). It should be noted that the Pds gene promoter is capable of directing transcription and therefore expression especially in chloroplasts and/or chromoplasts-containing tissues of plants. It should be further noted that the transit peptide encoded by part of the Pds coding sequence is capable of directing conjugated (i.e., in frame) proteins into plant chromoplasts and/or chloroplasts.

Figure 15:
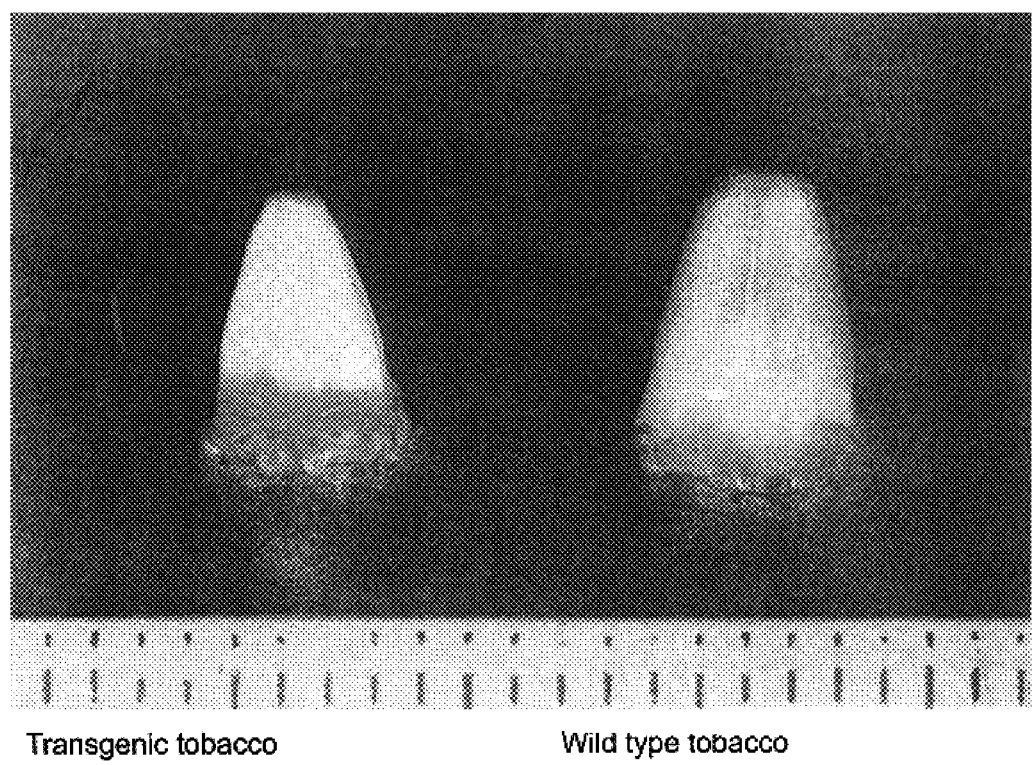
FIG. 15 shows a flower from a wild type tobacco plant and a flower from a transgenic tobacco plant according to the present invention.

As shown in FIG. 15, in chromoplasts-containing cells, such as in the nectary tissue of the flower of tobacco, this DNA construct induces accumulation of astaxanthin and other ketocarotenoids to a higher level which alters the color from the normal yellow to red.

Concentration and composition of carotenoids in chloroplasts-containing tissues, such as leaves, and in chromoplast-containing tissues, such as flowers, were determined in the transgenic plants and compared to normal non-transformed plants.

Carotenoids compositions in leaves (chloroplasts-containing tissue) and in the nectary tissue of flowers (chromoplast containing tissue) of wild type and transgenic tobacco plants were determined by thin layer chromatography (TLC) and by high pressure liquid chromatography (HPLC) as described above.

Total carotenoids concentration in leaves (chloroplasts-containing tissue) and in the nectary tissue of flowers (chromoplast containing tissue) of wild type and transgenic tobacco plants are summarized in Tables 3 below.

Percents of carotenoids composition in leaves of wild-type and transgenic tobacco plants are summarized in Tables 4 below.

Percents of carotenoids composition in the nectary tissue of flowers of wild-type and transgenic tobacco plants are summarized in Tables 5 below.

TABLE 3

| | μg carotenoids per gr fresh weight | |
| --- | --- | --- |
| | Wild-type | Transgenic with crtO |
| Leaf (Chloroplasts) | 200 | 240 |
| Nectary tissue (Chromoplasts) | 280 | 360 |

TABLE 4

| % of total carotenoids composition in chloroplasts-containing tissue (leaf) | | |
| --- | --- | --- |
| | Wild-type | Transgenic |
| β-carotene | 29.9 | 26.7 |
| neoxanthin | 5.0 | 5.9 |
| violaxanthin | 11.6 | 18.1 |
| antheraxanthin | 4.9 | 2.6 |
| lutein | 43.9 | 41.4 |
| zeaxanthin | 4.7 | 4.3 |
| astaxanthin + adonirubin | 0.0 | 1.0 |

TABLE 5

% of total caroteniod composition in chromoplasts-containing tissue (flower)

|  | Wild-type | Transgenic |
|---|---|---|
| beta-carotene | 58.1 | 21.0 |
| violaxanthin | 40.3 | 1.5 |
| lutein | 0.0 | 1.1 |
| zeaxanthin | 1.6 | 1.0 |
| hydroxyechinenone | 0.0 | 13.7 |
| 3'hydroxyechinenone | 0.0 | 4.1 |
| adonirubin | 0.0 | 22.4 |
| adonixanthin | 0.0 | 8.7 |
| astaxanthin | 0.0 | 26.5 |

Please note the elevated content of hydroxyechinenone, 3'hydroxyechinenone, adonirubin, adonixanthin and astaxanthin especially in the chromoplast containing tissue of the transgenic tobacco plants.

Thus, the present invention successfully addresses the shortcomings of the presently known configurations by enabling a relatively low cost biotechnological production of (3S,3'S) astaxanthin by providing a peptide having a β-C-4-oxygenase activity; a DNA segment coding for this peptide; an RNA segments coding for this peptide; a recombinant DNA molecule comprising a vector and the DNA segment; a host containing the above described recombinant DNA molecule or DNA segment; and of a method for biotechnologically producing (3S,3'S) astaxanthin or a food additive containing (3S,3'S) astaxanthin, using the host.

While the invention has been described with respect to a limited number of embodiments, it will be appreciated that many variations, modifications and other applications of the invention may be made.

What is claimed is:

1. An isolated nucleic acid comprising a nucleotide sequence at least 95% identical to SEQ ID NOs:1 or 2 said nucleotide sequence encoding a polypeptide having a β-carotene C-4-oxygenase activity.

2. The isolated nucleic acid of claim 1, wherein said nucleotide sequence includes a sequence as set forth in SEQ ID NOs:1 or 2.

3. The isolated nucleic acid of claim 1, wherein said nucleotide sequence includes a sequence as set forth between and including nucleotides 166 and 1152 of SEQ ID NOs:1 or 2.

4. A nucleic acid construct comprising the nucleic acid segment as of claim 1.

5. A host comprising the nucleic acid construct of claim 4, said host is selected from the group consisting of a microorganism and a plant.

6. A host comprising the nucleic acid of claim 1, said host is selected from the group consisting of a microorganism and a plant.

7. A food additive comprising the host of claim 5.

8. A food additive comprising the host of claim 6.

9. A transgenic plant expressing a transgene including a nucleotide sequence at least 95% identical to SEQ ID NO:1, said nucleotide sequence encoding a polypeptide having a β-carotene C-4-oxygenase activity.

10. The transgenic plant of claim 9, wherein said transgene includes a sequence as set forth in SEQ ID NO:1.

11. The transgenic plant of claim 9, wherein said transgene includes a sequence as set forth between and including nucleotides 166 and 1152 of SEQ ID NO:1.

12. A nucleic acid construct comprising a first polynucleotide encoding a polypeptide for directing a protein into plant chloroplasts or chromoplasts and an in frame second polynucleotide at least 95% identical to SEQ ID NOs:1 and encoding a polypeptide having β-carotene C-4-oxygenase activity.

13. The nucleic acid construct of claim 12, wherein said second polynucleotide includes a sequence as set forth in SEQ ID NO:1.

14. The nucleic acid construct of claim 12, wherein said second polynucleotide includes a sequence as set forth between and including nucleotides 166 and 1152 of SEQ ID NO:1.

15. The nucleic acid construct as in claim 12, wherein said first polynucleotide is derived from the Pds gene of tomato.

* * * * *